(12) United States Patent
Satake et al.

(10) Patent No.: US 6,329,396 B1
(45) Date of Patent: Dec. 11, 2001

(54) SUBSTITUTED BENZYLAMINOPIPERIDINE COMPOUNDS

(75) Inventors: Kunio Satake, Handa; Yuji Shishido, Aichi-ken; Hiroaki Wakabayashi, Kariya, all of (JP)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/562,144

(22) Filed: May 1, 2000

Related U.S. Application Data

(62) Division of application No. 09/011,271, filed as application No. PCT/IB96/00572 on Jun. 10, 1996, now abandoned.

(51) Int. Cl.$^7$ .................. C07D 211/56; A61K 31/445
(52) U.S. Cl. ................. 514/329; 546/192; 546/223
(58) Field of Search .................... 546/192, 223; 514/329

(56) References Cited

U.S. PATENT DOCUMENTS 5,990,125 * 11/1999 Howard ................. 514/305

FOREIGN PATENT DOCUMENTS

| 0610021 | 8/1994 | (EP) . |
|---|---|---|
| 0627221 | 12/1994 | (EP) . |
| 0653208 | 5/1995 | (EP) . |
| 0655246 | 5/1995 | (EP) . |
| WO 9217449 | 10/1992 | (WO) . |
| WO 92/17449 | * 10/1992 | (WO) . |
| WO 9300331 | 1/1993 | (WO) . |
| WO 9301170 | 1/1993 | (WO) . |

* cited by examiner

Primary Examiner—Mukund J. Shah
Assistant Examiner—Deepak R. Rao
(74) Attorney, Agent, or Firm—Peter C. Richardson; Paul H. Ginsburg; Roy F. Waldron

(57) ABSTRACT

The invention provides a substituted benzylaminopiperidine compounds that are useful in the treatment of gastrointestinal disorders; central nervous system (CNS) disorders; inflammatory disease; emesis; urinary incontinence; pain; migraine; sunburn; diseases, disorders and adverse conditions caused by *Heliobacter pylori*; or angiogenesis, especially CNS disorders in a mammalian subject, especially in humans.

5 Claims, No Drawings

SUBSTITUTED BENZYLAMINOPIPERIDINE COMPOUNDS

This application is a divisional application of application Ser. No. 09/011,271, filed May 1, 1998 now abandoned, which is the Section 371 National stage application of international application No. PCT/IB96/00572, filed Jun. 10, 1996.

TECHNICAL FILED

This invention relates to substituted benzylaminopiperidine compounds of interest to those in the field of medical chemistry and chemotherapy. More particularly, it is concerned with a series of substituted piperidine compounds, including their pharmaceutically acceptable salts, which are of special value in view of their ability to antagonize substance P. These compounds are of use in treating a gastrointestinal disorder, a central nervous system (CNS) disorder, an inflammatory disease, emesis, urinary incontinence, pain, migraine, sunburn, angiogenesis, diseases, disorders and adverse conditions caused by *Helicobacter pylori*, or the like, especially CNS disorders in a mammalian subject, especially humans.

BACKGROUND ART

Substance P is a naturally occurring undecapeptide belonging to the tachykinin family of peptides, the latter being so-named because of their prompt stimulatory action on smooth muscle tissue. More specifically, substance P is a pharmaceutically active neuropeptide that is produced in mammals (having originally been isolated from the gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine, as well as in central nervous system disorders such as anxiety and schizophrenia, in respiratory and inflammatory diseases such as asthma and rheumatoid arthritis, respectively, and in gastrointestinal disorders and diseases of GI tract, like ulcerative colitis and Crohn's diseases, etc. It is also reported that the tachykinin antagonists are useful for the treatment of allergic conditions, immunoregulation, vasodilation, bronchospasm, reflex or neuronal control of the viscera and senile dementia of the Alzheimer type, emesis, sunburn and *Helicobacter pylori* infection.

International Publication No. WO 93/01170, WO 93/00331 and WO 93/11110 disclose a wide variety of piperidine derivatives, as tachykinin antagonists such as substance P antagonists.

BRIEF DESCRIPTION OF THE INVENTION

The present invention provides substituted piperidine compounds of the following chemical formula (I):

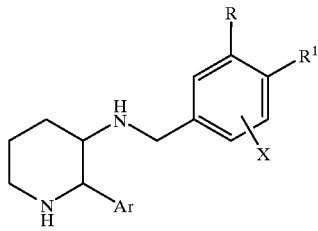

and its pharmaceutically acceptable salts, wherein

R is halo $C_1$–$C_8$ alkyl, halo $C_2$–$C_8$ alkenyl, halo $C_2$–$C_1$ alkynyl or halo $C_1$–$C_8$ alkyl substituted by hydroxy or $C_1$–$C_8$ alkoxy; $R^1$ is hydrogen, halo or $C_1$–$C_6$ alkoxy; or R and $R^1$, together with the two carbon atoms shared between the benzene ring and the R and $R^1$, complete a fused $C_4$–$C_6$ cycloalkyl wherein one carbon atom is optionally replaced by oxygen and wherein one or two of the carbon atoms are optionally substituted by up to five substituents selected from halo, $C_1$–$C_6$ alkyl and halo $C_1$–$C_6$ alkyl;

X is $C_1$–$C_6$ alkoxy, halo $C_1$–$C_6$ alkoxy, phenoxy or halo; and

Ar is phenyl optionally substituted by halo.

The piperidine compounds of the present invention of formula (I) exhibit good antagonist activity toward Substance P, particularly good activity against CNS disorders, and are thus useful for treatment of a gastrointestinal disorder, a central nervous system disorder, an inflammatory disease, emesis, urinary incontinence, pain, migraine, sunburn, angiogenesis, diseases, or disorders and adverse conditions caused by *Helicobacter pylori* in a mammalian subject, especially humans.

Accordingly, the present invention provides a pharmaceutical composition for the treatment of a gastrointestinal disorder, a central nervous system disorder, an inflammatory disease, emesis, urinary incontinence, pain, migraine, sunburn, angiogenesis, diseases disorders and adverse conditions caused by *Helicobacter pylori*, or the like, especially CNS disorders in a mammalian subject, especially humans, which comprises a therapeutically effective amount of a compound of the formula (I) together with a pharmaceutically acceptable carrier.

DETAILED DESCRIPTION OF THE INVENTION

In this specification, the term "halo $C_1$–$C_8$ alkyl" is used herein to mean a straight, branched or cyclic $C_1$–$C_8$ alkyl radical substituted with one or more halogens (i.e., Cl, F, I or Br) including, but not limited to, trifluoromethyl, difluoroethyl, trifluoroethyl, pentafluoroethyl, trifluoroisopropyl, tetrafluoroisopropyl, pentafluoroisopropyl, hexafluoroisopropyl or heptafluoroisopropyl and the like;

the term "halo $C_2$–$C_8$ alkenyl" is used herein to mean a straight, branched or cyclic $C_2$–$C_8$ alkenyl radical substituted with one or more halogens (i.e., Cl, F, I or Br) including, but not limited to, 3,3,3-trifluoropropenyl, 1,1-dimethyl-4,4,4-trifluorobutenyl and the like;

the term "halo $C_2$–$C_8$ alkynyl" is used herein to mean a straight, branched or cyclic $C_2$–$C_8$ alkynyl radical substituted with one or more halogens (i.e., Cl, F, I or Br)

including, but not limited to, 3,3,3-trifluoropropynyl, 1,1-dimethyl-4,4,4-trifluorobutynyl and the like; and the term "halo $C_1$–$C_8$ alkoxy" is used herein to mean a straight, branched or cyclic $C_1$–$C_8$ alkoxy radical substituted with one or more halogens (i.e., Cl, F, I or Br) including, but not limited to, difluoromethoxy, trifluoromethoxy, 2,2,2-trifluoroethoxy and the like.

In the chemical formula (I):

R is preferably $C_1$–$C_6$ alkyl, hydroxy $C_1$–$C_6$ alkyl, $C_2$–$C_6$ alkenyl or $C_2$–$C_6$ alkynyl, wherein the alkyl, alkenyl and alkynyl moieties are substituted by two to seven halogen atoms.

In preferable embodiment of the present invention, R is $C_1$–$C_6$ alkyl, hydroxy $C_1$–$C_6$ alkyl, $C_2$–$C_6$ alkenyl or $C_2$–$C_6$ alkynyl, preferably $C_1$–$C_6$ alkyl, these groups being substituted by two to three fluorine atoms. Examples of R are trifluoromethyl, difluoroethyl, trifluoroethyl, trifluoroisopropyl, trifluoro-tert-butyl, trifluoro-1,1-dimethylmethyl-3-butynyl, and 2-chlorotrifluoroisopropyl.

In another preferable embodiment of the present invention, R is $C_1$–$C_6$ alkyl, hydroxy $C_1$–$C_6$ alkyl, $C_2$–$C_6$ alkenyl or $C_2$–$C_6$ alkynyl, these groups being substituted by four to seven fluorine atoms. Examples of R are pentafluoroethyl, pentafluoropropyl, pentafluoroisopropenyl, hexafluoroisopropyl, heptafluoroisopropyl, hexafluoro-2-hydroxyisopropyl and hexafluoro-tert-butyl.

$R^1$ is preferably hydrogen or methoxy, more preferably hydrogen.

In another preferable embodiment of the present invention, R and $R^1$ may be taken together with the two carbon atoms shared between the benzene ring and the R and $R^1$, to complete fused $C_4$–$C_6$ cycloalkyl wherein one carbon atom is optionally replaced by oxygen. The one or two of the carbon atoms of the $C_4$–$C_6$ cycloalkyl may be optionally substituted by up to four, more preferably one to two, substituents selected from a fluorine atom and trifluoromethyl. More preferably, R and $R^1$, may be taken together with the two carbon atoms shared between the benzene ring and the R and $R^1$, complete trifluoromethylcyclopentyl, trifluoromethylcyclohexyl, difluorocyclohexyl or difluorodimethylcyclohexyl.

X is preferably halo, methoxy, difluoromethoxy, trifluoromethoxy or phenoxy, more preferably methoxy, difluoromethoxy or trifluoromethoxy, most preferably methoxy. X is preferably at 2-position on the phenyl ring.

Ar is preferably phenyl.

Another preferred group of compounds of this invention includes the compounds of formula (Ia):

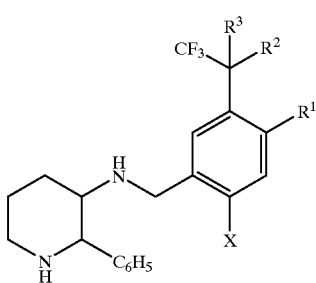

(Ia)

wherein $R^1$ is hydrogen, halo or methoxy; and $R^2$ and $R^3$ is independently selected from halo, $C_1$–$C_6$ alkyl, $C_2$–$C_6$ alkenyl and $C_2$–$C_6$ alkynyl, or $R^2$ and $R^3$ together complete $C_2$–$C_6$ alkylidene, wherein the alkyl, alkenyl, alkynyl and alkylidene moiety are optionally substituted by up to seven halogen atoms;

or $R^1$ and $R^2$ are taken together to complete a fused $C_4$–$C_6$ cycloalkyl wherein one carbon atom is optionally replaced by oxygen, the $C_4$–$C_6$ cycloalkyl being optionally substituted by up to four substituents selected from halo, $C_1$–$C_4$ alkyl, and halo $C_1$–$C_4$ alkyl.

In these compounds, preferable stereochemistry of 2-aryl and 3-benzylamino is (2S, 3S).

A preferred group of individual compounds of this invention are the following:

(2S,3S)-3-(2-Fluoro-5-(trifluoromethyl)benzyl)amino-2-phenylpiperidine or its salts;
(2S,3S)-3-(2-Chloro-5-(trifluoromethyl)benzyl)amino-2-phenylpiperidine or its salts;
(2S,3S)-3-(2-Methoxy-5-(trifluoromethyl)benzyl)amino-2-phenylpiperidine or its salts;
(2S,3S)-3-(2-Phenoxy-5-(trifluoromethyl)benzyl)amino-2-phenylpiperidine or its salts;
(2S,3S)-3-(5-(1,1-Difluoroethyl)-2-(trifluoromethoxy)benzyl)amino-2-phenylpiperidine or its salts;
(2S,3S)-3-(5-(1,1-Difluoroethyl)-2-methoxybenzyl)amino-2-phenylpiperidine or its salts;
(2S,3S)-3-(2-Methoxy-5-(2,2,2-trifluoroethyl)benzyl)amino-2-phenylpiperidine or its salts;
(2S,3S)-3-(2-Methoxy-5-(1-(trifluoromethyl)ethyl)benzyl)amino-2-phenylpiperidine or its salts;
(2S,3S)-3-[5-(1,1-dimethyl-4,4,4-trifluoro-2-butynyl)-2-methoxybenzyl]amino-2-phenylpiperidine or its salts;
(2S,3S)-3-[5-(1,1-Dimethyl-2,2,2-trifluoroethyl)-2-methoxybenzylamino]-2-phenylpiperidine or its salt;
(2S,3S)-3-(2,4-Dimethoxy-5-(2,2,2-trifluoroethyl)benzyl)amino-2-phenylpiperidine or its salts; and
(2S,3S)-3-[5-(1-Chloro-1-(trifluoromethyl-ethyl)-2-methoxybenzylamino]-2-phenylpiperidine or its salts.

Another preferred group of individual compounds of this invention are the following:

(2S,3S)-2-Phenyl-3-(5-(2,2,2-trifluoro-1-(trifluoromethyl)ethyl)-2-methoxybenzyl)aminopiperidine or its salts;
(2S,3S)-2-Phenyl-3-(5-(2,2,2-trifluoro 1-(trifluoromethyl)ethyl)-2-methoxybenzyl)aminopiperidine or its salts;
(2S,3S)-2-Phenyl-3-(5-(1,2,2,2-tetrafluoro-1-(trifluoromethyl)ethyl)-2-methoxybenzyl)aminopiperidine or its salts;
(2S,3S)-3-(2-Methoxy-5-(1,1,2,2,2-pentafluoroethyl)benzyl)amino-2-phenylpiperidine or its salts;
(2S,3S)-2-Phenyl-3-(5-(2,2,2-trifluoro-1-methyl-1-(trifluoromethyl)ethyl)-2-methoxybenzyl)aminopiperidine or its salts;
(2S,3S)-3-[5-[2,2-Difluoro-1-(trifluoromethyl)ethenyl]-2-methoxybenzyl]amino-2-phenylpiperidine or its salts; and
(2S,3S)-3-(2-Methoxy-5-(2,2,2-trifluoro-1-hydroxy-1-(trifluoromethyl)ethyl)benzyl)amino-2-phenylpiperidine or its salts.

Another preferred group of individual compounds of this invention are the following:

[(2S,3S)-3-[5-Methoxy-1-(trifluoromethyl-indan-6-yl-methylamino]-2-phenylpiperidine or its salts;
(2S,3S)-3-[6-Methoxy-1-(trifluoromethyl-1,2,3,4-tetrahydronaphthalen-7-yl-methylamino]-2-phenylpiperidine or its salts; and (2S,3S)-3-((2,2-Difluoro-6-methoxy-1,2,3,4-tetrahydronaphthalen-7-yl)methyl)amino-2-phenylpiperidine or its salts.

General Synthesis

The piperidine compounds of the formula (I) of this invention may be prepared as described in the following reaction schemes.

Unless otherwise indicated, in the reaction schemes that follow, R, X and Ar are defined as above.

Scheme A-I

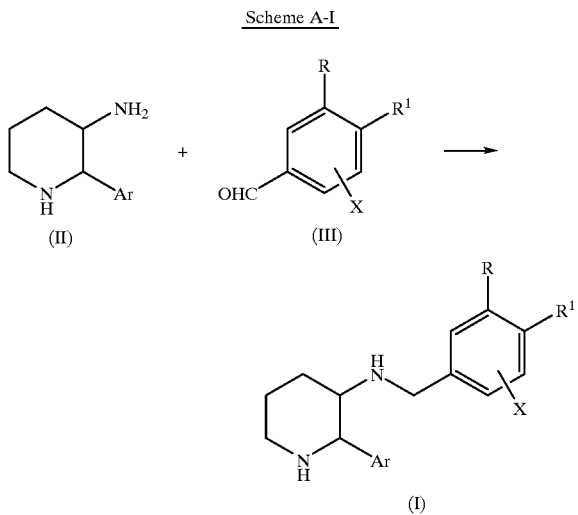

Scheme A-I illustrates a method for preparing compounds of the formula (I) by reductive amination of a compound of the formula (III) with a compound (II). The reduction can be carried out by catalytic hydrogenation, or with several hydride reagents in a reaction-inert solvent. The catalytic hydrogenation may be carried out in the presence of a metal catalyst such as palladium or Raney nickel. Suitable hydride reagents include borohydrides such as sodium borohydride (NaBH$_4$), sodium cyanoborohydride (NaBH$_3$CN) and sodium triacetoxyborohydride (NaB(OAc)$_3$H), boranes, aluminum-based reagents and trialkylsilanes. Suitable solvents include polar solvents such as methanol, ethanol, methylene chloride, tetrahydrofuran (THF), dioxane and ethylacteate. This reaction is typically carried out at a temperature from −78° C. to reflux temperature of the solvent, preferably from 0° C. to 25° C. for 5 minutes to 48 hours, preferably from 0.5 to 12 hours.

Alternatively, the piperidine compounds of the formula (I) of this invention may be prepared as shown in the following scheme A-II.

Scheme A-II

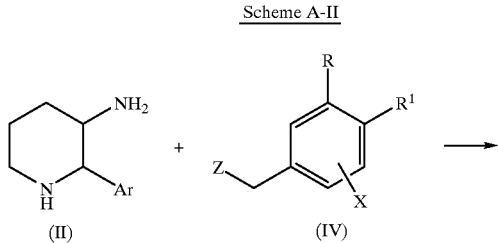

-continued

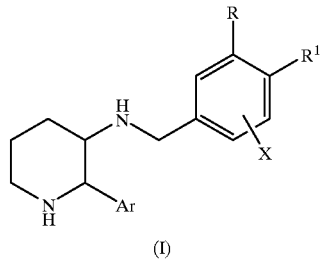

(wherein Z is a leaving group such as halo or sulfonate including tosylate or mesylate)

Referring to Scheme A-II, the compounds of the formula (I) of this invention may be prepared by a reaction of a compound of the formula (IV) with a compound (II). The compound (IV) may be treated with compound (II) in the presence of a base (e.g., K$_2$CO$_3$ or Na$_2$CO$_3$) in a polar solvent (e.g., methanol, ethanol, isopropylalcohol, THF, dioxane, dimethylformamide (DMF) or dimethylsulfoxide (DMSO). This reaction is typically carried out at a temperature from −78° C. to reflux temperature of the solvent, preferably from 0° C. to 25° C. for 5 minutes to 48 hours, preferably from 0.5 to 12 hours.

The compounds (IV) may be prepared by reduction of an aldehyde of the formula (III), followed by conversion of a hydroxy group of the resultant compound into a leaving group, Z. Reduction of the aldehyde (III) may be accomplished using a variety of reducing agents in a reaction-inert solvent. Suitable reducing agent/solvent systems include sodium tetrahydroborate (NaBH$_4$) in methanol or ethanol; lithium tetrahydroborate (LiBH$_4$) in THF or diethyl ether; lithium tetrahydroaluminum (LiAlH$_4$), lithium triethoxyhydroaluminum (LiAl(OEt)$_3$H) lithium tert-buthoxyhydroaluminum (LiAl(OBut)$_3$H) or aluminum trihydride (AlH$_3$) in THF or diethyl ether; and iso-butyl aluminum hydride(i-BuAlH$_2$) or diisopropyl aluminum hydride (DIBAL-H) in dichloromethane, THF or n-hexane. This reaction is generally carried out at a temperature from −20° C. to 25° C. for 5 minutes to 12 hours. Then, the hydroxy group of the resultant compound is converted to a leaving group, Z (e.g., halo such as chloro, bromo, iodo or fluoro, or sulfonate including tosylate or mesylate). Conversion of the hydroxy group into the leaving group, Z may be accomplished according to methods known to those skilled in the art. For example, when Z is sulfonate such as tosylate or mesylate, the hydroxy compound is reacted with sulfonate in the presence of pyridine or triethylamine in dichloromethane. When Z is halo such as chloro or bromo, the hydroxy compound may be treated with SOX$_2$ (X is Cl or Br) in the presence of pyridine.

The compounds of the formula (III) can be prepared as illustrated in the following scheme B-I.

Scheme B-I

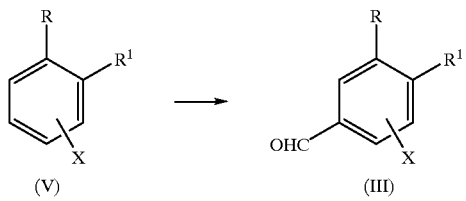

The compounds of the formula (III) may be prepared by direct or indirect formylation of a compound of the formula (V). Any formylation methods known to those skilled in the art may be used, to introduce a formyl group into a benzene ring. For example, direct formylation may be accomplished by contacting the compound (V) with a suitable formylating agent in the presence of a suitable catalyst. Suitable formylating agent/catalyst systems include dichloromethyl methyl ether/titanium (IV) chloride ($Cl_2CHOCH_3/TiCl_4$), trifluoroacetic acid ($CF_3CO_2H$)/hexamethylenetetramine (modified Duff's conditions) and phosphoryl trichloride ($POCl_3$)/DMF (Vilsmeier's conditions). Indirect formylation may be achieved by halogenating the compound (V), displacing the halogen atom introduced with a cyano group, and then subjecting the resultant cyano-substituted compound to reduction. The halogenation as used herein may be carried out according to the procedure reported in G. A. Olah et., al. *J. Org Chem,* 58, 3194 (1993). The displacement of the halogen atom with a cyano group may be performed according to the methods reported in D. M. Tschaem et. al., *Synth Commun,* 24, 887 (1994), K. Takagi et. al., 64 *Bull Chem. Soc. Jpn.* 64, 1118 (1991). The reduction as used herein may be performed in the presence of diisopropyl aluminiumhydride (DIBAL-H) in dichloromethane or Raney nickel in formic acid.

The starting materials of the formula (V) are known compounds which are commercially available, or can be prepared by known methods. For example, compounds of the formula (V) wherein X is alkoxy can be prepared by O-alkylation of the corresponding compounds (V) wherein X is hydroxy, in the presence of a base (e.g., NaH or KH) in a suitable solvent (e.g., DMSO, DMF and THF).

Compound (V) can be also prepared by other methods as described in the following literature:

(A) trifluoromethylation, *J. Am. Chem Soc.,* 111, 393–395 (1989);

(B) tert-alkylation, *Angew. Chem. Int. Ed. Engl.* 19, No.11 900–901 (1980); or (C) chemoselective and position specific methylation of tert-alkyl halides with methyltitanium (IV), *Angew. Chem. Int. Ed. Engl.* 19, No.11 901–902 (1980) and fluorination of keton, *Organic Reaction* (1988), 35.

In addition, R in the compound of formula (III) can be converted to any desirable substituent R'' (e.g., $CF_2CF_3$ or $CF_2CH_3$) according to techniques known to a person skilled in the art, for example, as indicated in the following Scheme B-II.

Scheme B-II

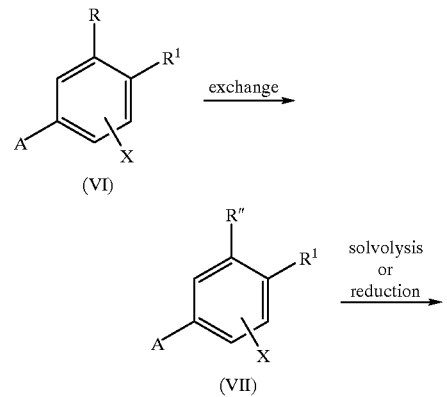

A = acetal, CN, etc...

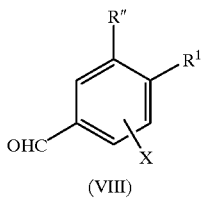

In Scheme B-II, the starting materials of the formula (VI) are known compounds which can be prepared according to the procedures described in, for example *Collect. Czech. Chem. Commun.,* 52, 980 (1987) or *Bull. Chem. Soc. Jpn.,* 51, 2435 (1978).

For example, a compound of formula (VI) wherein A is CN and R is alkylcarbonyl (see *Collect. Czech. Chem. Commun.,* 52, 980 (1987)) may be subjected to thioketalization followed by substitution to obtain a compound of formula (VII) (see *J. Org. Chem.,* 51, 3508 (1986)). A compound of formula (VI) wherein A is acetal and R is halo (see *Bull. Chem. Soc. Jpn.,* 51, 2435 (1978)) may be subjected to alkylation to obtain a compound of formula (VII) (see *Synthetic Comm.,* 18, 965 (1988)).

Then the compound of formula (VII) may be subjected to solvolysis or reduction under suitable reaction conditions to obtain a compound of formula (VIII) wherein R is converted to R'' (e.g., $CF_2CF_3$ or $CF_2CH_3$) (see *J. Org. Chem,* 24, 627 (1959) and *Protective group in organic synthesis,* John Wiley & sons, inc., 180 and 191 (1991)).

Alternatively, compounds of the formula (I) may be prepared as shown in the following Scheme A-III.

Scheme A-III

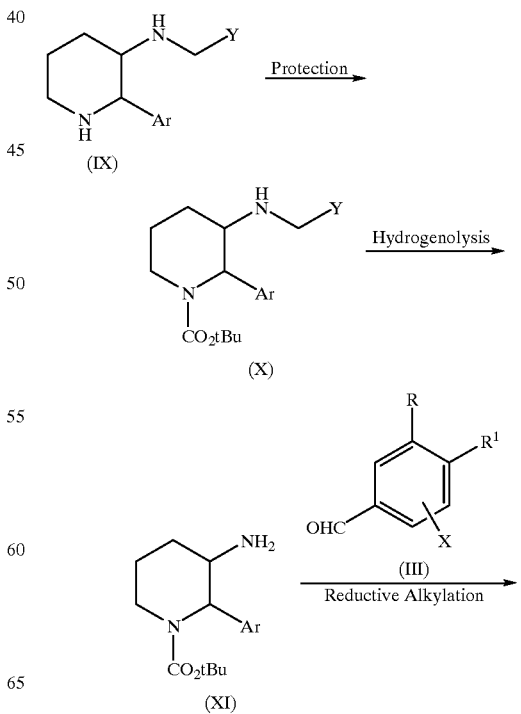

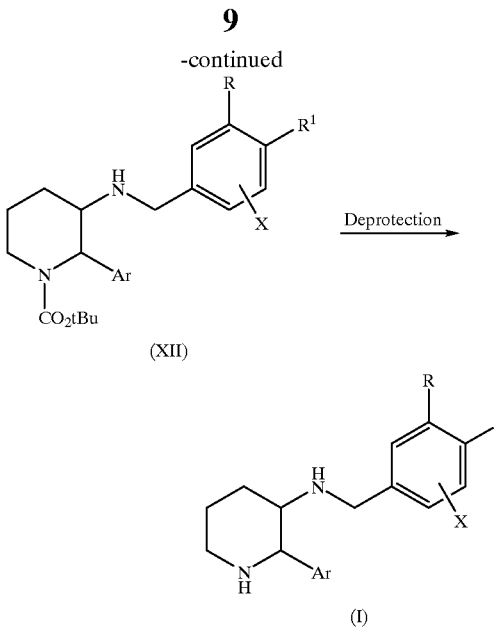

Scheme A-III illustrates the preparation of compounds of the formula (I). Referring to Scheme A-III, N-protection of a compound of the formula (IX) (Ar is phenyl or the like) may be carried out by treatment with (t-BuOCO)$_2$O(Boc$_2$O) in the presence of a base such as sodium bicarbonate (NaHCO$_3$) or triethylamine (Et$_3$N) to obtain a compound of the formula (X). Compound (X) is subjected to hydrogenolysis to obtain a compound of the formula (XI) (wherein Ar is phenyl). An alternative route for N-protection of a compound of the formula (IX) may be carried out by treatment with carbobenzoxy chloride (Cbz-Cl) in the presence of a base such as sodium bicarbonate (NaHCO$_3$) or triethylamine (Et$_3$N), wherein Ar is phenyl. The hydrogenolysis may be carried out by treatment with H$_2$ or ammonium formate (HCO$_2$NH$_4$) in the presence of a metal catalyst such as a palladium on charcoal (e.g. 20% palladium on charcoal) in a suitable solvent. Then, the compound (XI) is subjected to the reductive amination as described in Scheme A-I. The compound (XII) may be converted into a compound of the formula (I) by treatment with acid catalyst such as hydrochloride (HCl) in methanol, conc.HCl in ethylacetate or CF$_3$CO$_2$H in dichloroethane.

The compounds of formula (I), and the intermediates shown in the above reaction schemes can be isolated and purified by conventional procedures, such as recrystallization or chromatographic separation.

As the piperidine compounds of this invention possess at least two asymmetric centers, they are capable of occurring in various stereoisomeric forms or configurations. Hence, the compounds can exist in separated (+)- and (−)-optically active forms, as well as mixtures thereof. The present invention includes all such forms within its scope. Individual isomers can be obtained by known methods, such as optical resolution, optically selective reaction, or chromatographic separation in the preparation of the final product or its intermediate.

In so far as the piperidine compounds of this invention are basic compounds, they are all capable of forming a wide variety of different salts with various inorganic and organic acids. Although such salts must be pharmaceutically acceptable for administration to animals, it is often desirable in practice to initially isolate the piperidine base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the piperidine base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained. The acid which are used to prepare the pharmaceutically acceptable acid addition salts of the aforementioned piperidine base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bitartrate succinate, maleate, fumarate, gluconate, saccharate, benzoate, methanesulfonate, ethanesulfonate, benzenesulfonate, p-toluenesulfonate and pamoate (i.e., 1.1'-methylene-bis-(2-hydroxy-3-naphthoate))salts.

The piperidine compounds of the invention which have also acidic groups are capable of forming base salts with various pharmaceutically acceptable cations. Examples of such salts include the alkali metal or alkaline-earth metal salts and particularly, the sodium and potassium salts. These salts are all prepared by conventional techniques.

The chemical bases which are used as reagents to prepare the pharmaceutically acceptable base salts of this invention are those which form non-toxic base salts with the herein described acidic piperidine derivatives. These particular non-toxic base salts include those derived form such pharmaceutically acceptable cations as sodium, potassium, calcium and magnesium, etc. These salts can easily be prepared by treating the aforementioned acidic piperidine compounds with an aqueous solution containing the desired pharmaceutically acceptable cation, and then evaporating the resulting solution to dryness, preferably under reduced pressure. Alternatively, they may also be prepared by mixing lower alkanoic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The active piperidine compounds of the present invention exhibit significant substance P receptor-binding activity and therefore, are of value in the treatment of a wide variety of clinical conditions which are characterized by the presence of an excess of said substance P activity. Such conditions include gastrointestinal disorders, central nervous system disorders, inflammatory diseases, emesis, urinary incontinence, pain, migraine or angiogenesis in a mammalian subject, especially humans. For treatment of emesis, these compounds may preferably be used in combination with a 5HT$_3$ receptor antagonist.

The active piperidine compounds of the formula (I) of this invention can be administered via either the oral, parenteral or topical routes to mammals. In general, these compounds are most desirably administered to humans in doses ranging from about 0.3 mg up to 750 mg per day, although variations will necessarily occur depending upon the weight and condition of the subject being treated and the particular route of administration chosen. However, a dosage level that is in the range of from about 0.06 mg to about 2 mg per kg of body weight per day is most desirably employed. Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects provided that such higher dose levels are first divided into several small doses for administration throughout the day.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging about 5.0% to about 70% by weight.

For oral administration, tablets containing various excipient such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention, as substance P antagonists, is determined by their ability to inhibit the binding of substance P at its receptor sites in CHO-cells which reveal NK1 receptor or IM-9 cells employing radioactive ligands. The substance P antagonist activity of the herein described piperidine compounds is evaluated by using the standard assay procedure described by M. A. Cascieri et al., as reported in *The Journal of Immunology*, 133, 3260 (1984). This method essentially involves determining the concentration of the individual compound required to reduce by 50% the amount of radio-labelled substance P ligands at their receptor sites in said isolated cow tissues or IM-9 cells, thereby affording characteristic $IC_{50}$ values for each compound tested. More specifically, inhibition of [$^3$H]SP binding to human IM-9 cells by compounds are determined in assay buffer (50 mM Tris-HCl (pH 7.4), 1 mM $MnCl_2$, 0.02% bovine serum albumin, bacitracin (40 µg/ml), leupeptin (4 µg/ml), chymostatin (2 µg/ml) and phosphoramidon (30 µg/ml)). The reaction is initiated by the addition of cells to assay buffer containing 0.56 nM [$^3$H]SP and various concentrations of compounds (total volume; 0.5 ml) and allowed to incubate for 120 min at 4° C. Incubation is terminated by filtration onto GF/B filters (presoaked in 0.1% polyethylenimine for 2 hours). Nonspecific binding is defined as the radioactivity remaining in the presence of 1 µM SP. The filters are placed into tubes and counted using liquid scintillation counter.

The adverse effect on $Ca^{2+}$ channel binding affinity is determined by study of verapamil binding in a rat heart membrane preparation. More specifically, verapamil binding is performed as previously described by Reynolds et al., (*J. Pharmacol. Exp. Ther.* 237, 731, 1986). Briefly, incubations are initiated by the addition of tissue to tubes containing 0.25 nM [$^3$H]desmethoxyverapamil and various concentrations of compounds (total volume; 1 ml). Nonspecific binding is defined as radioligand binding remaining in the presence of 3–10 µM methoxyverapamil.

The activity of the compounds of this invention against CNS disorders is determined in a [$Sar^9$, $Met(O_2)^{11}$] substance P-induced tapping test in gerbils. More specifically, gerbils are lightly anesthetized with ether and the skull surface is exposed. [$Sar^9$, $Met(O_2)^{11}$]substance P or vehicle (5 µl) are administered directly into the lateral ventricles via a 25 gauge needle inserted 3.5 mm below lambda. Following injection, gerbils are placed in 2 l beaker individually and monitored for repetitive hind paw tapping. Some compounds prepared in the following Examples were tested in accordance with these testing methods. As a result, it was found that the compounds of the present inventions have good antagonist activity toward Substance P, particularly good activity against CNS disorders with favorable metabolical properties. More specifically, for example, by comparing trifluoromethyl- and hexafluoroisopropyl-benzylaminopiperidine compounds (Examples 3 and 5, respectively) with the corresponding no halo-substituted compounds, it was found that the halo-substituted compounds showed unexpectedly improved activity against CNS disorders.

The half life of the compounds of this invention is determined in a human liver microsome preparation. More specifically, the compound (1 µM) was incubated with pooled human liver microsome (2.0 mg/ml), NADP (1.3 mM), NADH (0.93 mM), glucose-6-phosphate (3.3 mM) $MgCl_2$ (3.3 mM), and glucose-6-phosphate dehydrogenase (8 units/ml) in a total volume of 1.2 ml 100 mM potassium phosphate buffer, pH 7.4. At various time points (0, 5, 10, 30 and 60 min), a 100 µl sample was added to acetonitrile solution (1.0 ml), which included an internal standard. The precipitated protein was spun down in a centrifuge (3,000×g, 5 min). The supernatant w as analyzed by LC-MS. LC-MS unit was consisted of Hewlett Packard HP1090 HPLC system and Sciex API-III. Samples(10 μl) were injected by means of autosampler, onto Hewlett Packard ODS-Hypersil column (2.1×20 mm). A mobile phase was consisted of 80% acetonitrile in 10 mM ammonium acetate. The measurement of API-III was analyzed with multiple reacting monitoring (MRM) detection.

EXAMPLE 1

Preparation of (2S, 3S)-3-(2-Fluoro-5-(trifluoromethyl)benzyl)amino-2-phenylpiperidine dihydrochloride (Compound 2)

(i) (2S, 3S)-2-Phenylpiperidin-3-amine dihydrochloride (Compound 1 )

This compound was prepared according to the procedures disclosed in EP-558156.

(ii) (2S, 3S )-3-(2-Fluoro-5-(trifluoromethyl)benzyl)amino-2-phenylpiperidine dihydrochloride (Compound 2)

To a stirred suspension of Compound 1 (150 mg, 0.60 mmol) and 2-fluoro-5-(trifluoromethyl)benzaldehyde (116 mg, 0.60 mmol) in dry $CH_2Cl_2$ (6 ml) was added $NaBH(OAc)_3$ (179 mg, 0.84 mmol) portionwise under nitrogen at room temperature. The reaction mixture was stirred at room temperature for 6.5 hr. This was basified with sat. $NaHCO_3$ aq., extracted with $CH_2Cl_2$, dried with $MgSO_4$, and concentrated to give crude (2S, 3S)-3-(2-fluoro-5-(trifluoromethyl)benzyl)amino-2-phenylpiperidine as a colorless oil. This was purified with chromatography to give pure (2S, 3S)-3-(2-fluoro-5-(trifluoromethyl)benzyl)amino-2-phenylpiperidine as a colorless oil (75 mg). This was diluted with ethyl acetate, added HCl-MeOH, and concentrated. The white solid was recrystallized from MeOH-ether to give Compound 2 as a white crystalline (67 mg, 26.3%).

mp 195–203° C.

$^1$H-NMR (CDCl$_3$, free base) 7.42–7.22 (m, 7H), 6.99 (t, J=8.8 Hz, 1H), 3.90 (d, J=2.2 Hz, 1H), 3.61 (d, J=15.0 Hz, 1H), 3.46 (d, J=15.0 Hz, 1H), 3.28–3.22 (m, 1H), 2.86–2.76 (m, 2H), 2.08–2.03 (m, 1H), 1.95–1.78 (m, 1H), 1.69–1.57 (m, 1H), 1.48–1.44 (m, 1H)

EXAMPLE 2

Preparation of (2S, 3S)-3-(2-Chloro-5-(trifluoromethyl)benzyl)amino-2-phenylpiperidine dihydrochloride (Compound 3)

To a stirred suspension of Compound 1 (150 mg, 0.60 mmol) and 2-chloro-5-(trifluoromethyl)benzaldehyde (126 mg, 0.60 mmol) in dry $CH_2Cl_2$ (6 ml) was added $NaBH(OAc)_3$ (179 mg, 0.84 mmol) portionwise under nitrogen at room temperature. The reaction mixture was stirred at room temperature for 17 hr. This was basified with sat. $NaHCO_3$ aq., extracted with $CH_2Cl_2$, dried with $MgSO_4$, and concentrated to give crude (2S, 3S)-3-(2-chloro-5-(trifluoromethyl)benzyl)amino-2-phenylpiperidine as a colorless oil. This was purified with chromatography to give pure (2S, 3S)-3-(2-chloro-5-(trifluoromethyl)benzyl)amino-2-phenylpiperidine as a colorless oil (135 mg). This was diluted with ethyl acetate, added HCl-MeOH, and concentrated. The white solid was recrystallized from MeOH to give Compound 3 as a white crystalline (64 mg, 24.1%).

mp 200–210° C.

$^1$H-NMR (CDCl$_3$, free base) 7.40–7.22 (m, 8H), 3.91 (d, J=2.2 Hz, 1H), 3.66 (d, J=15.0 Hz, 1H), 3.50 (d, J=15.0 Hz, 1H), 3.29–3.23 (m, 1H), 2.86–2.76 (m, 2H), 2.10–2.05 (m, 1H), 1.97–1.80 (m, 1H), 1.70–1.58 (m, 1H), 1.51–1.45 (m, 1H)

EXAMPLE 3

Preparation of (2S, 3S)-3-(2-Methoxy-5-(trifluoromethyl)benzyl)amino-2-phenylpiperidine dihydrochloride (Compound 5)

(i) 2-Methoxy-5-(trifluoromethyl)benzaldehyde (Compound 4)

To a stirred and ice-cooled solution of NaOMe (904 mg, 4.68 mmol) was added 2-fluoro-5-(trifluoromethyl)benzaldehyde (500 mg, 2.60 mmol) portionwise. The dropping funnel employed was washed with THF. The resultant suspension was stirred at room temperature for 5 hr. The reaction mixture was neutralizing for acetic acid (0.3 ml, 5.0 mmol), the solvent was removed. To the solid residue was added water and the mixture was extracted with $CH_2Cl_2$. The combined $CH_2Cl_2$ extracts were washed with sat. $NaHCO_3$ aq., dried with $MgSO_4$, and concentrated to give crude Compound 4 as a white solid. This was purified with preparative TLC to give pure Compound 4 as a white crystalline (363 mg, 68.4%).

$^1$H-NMR(CDCl$_3$) 10.47(s, 1H), 8.11(d, J=2.2 Hz, 1H), 7.80(dd, J=8.8, 2.2 Hz, 1H), 7.10(d, J=8.8 Hz, 1H), 4.01(s, 3H)

(ii) (2S, 3S)-3-(2-Methoxy-5-(trifluoromethyl)benzyl)amino-2-phenylpiperidine dihydrochloride (Compound 5)

To a stirred suspension of Compound 1 (150 mg, 0.60 mmol) and Compound 4 (123 mg, 0.60 mmol) in dry $CH_2Cl_2$ (6 ml) was added $NaBH(OAc)_3$ (179 mg, 0.84 mmol) portionwise under nitrogen at room temperature. The reaction mixture was stirred at room temperature for 3.5 hr. This was basified with sat. $NaHCO_3$ aq., extracted with $CH_2Cl_2$, dried with $MgSO_4$, and concentrated to give crude (2S, 3S)-3-(2-methoxy-5-(trifluoromethyl)benzyl)amino-2-phenylpiperidine as a colorless oil. This was purified with chromatography to give pure (2S, 3S)-3-(2-methoxy-5-(trifluoromethyl)benzyl)amino-2-phenylpiperidine as a colorless oil (95 mg). This was diluted with ethyl acetate, added HCl-MeOH, and concentrated. The white solid was recrystallized from MeOH-ether to give Compound 5 as a white crystalline (85 mg, 32.4%).

mp 228–233° C.

$^1$H-NMR(CDCl$_3$, free base) 7.40 (d, J=8.8 Hz, 1H), 7.34–7.23 (m, 6H), 6.71 (d, J=8.8 Hz, 1H), 3.92 (d, J=2.2 Hz, 1H), 3.66 (d, J=14.3 Hz, 1H), 3.52 (s, 3H), 3.42 (d, J=14.3 Hz, 1H), 3.33–3.29 (m, 1H), 2.87–2.77 (m, 2H), 2.12–1.90 (m, 2H), 1.66–1.56 (m, 1H), 1.48–1.43 (m, 1H)

EXAMPLE 4

Preparation of (2S, 3S)-3-(2-Phenoxy-5-(trifluoromethyl)benzyl)amino-2-phenylpiperidine dihydrochloride (Compound 7)

(i) 2-Phenoxy-5-(trifluoromethyl)benzaldehyde (Compound 6)

To a stirred solution of 2-chloro-5-(trifluoromethyl)benzaldehyde (500 mg, 2.40 mmol) in DMF (5 ml) was added phenol (226 mg, 2.40 mmol), $K_2CO_3$ (663 mg, 4.79 mmol). The reaction suspension was stirred at room temperature for 1 hr, then at 80° C. for 1.5 hr. The reaction mixture was neutralizing for acetic acid (0.5 ml), the solvent was removed. To the solid residue was added water and the mixture was extracted with $CH_2Cl_2$. The combined $CH_2Cl_2$ extracts were washed with sat. $NaHCO_3$ aq., dried with $MgSO_4$, and concentrated to give crude Compound 6 as a yellow oil. This was purified with chromatography to give pure Compound 6 as a yellow oil (466 mg, 72.9%)

$^1$H-NMR(CDCl$_3$) 10.58(s, 1H), 8.21(d, J=2.6 Hz, 1H), 7.70(dd, J=8.8, 2.6 Hz, 1H), 7.50–7.42 (m, 2H), 7.31–7.25 (m, 1H), 7.16–7.10 (m, 2H), 6.93(d J=8.8 Hz, 1H)

(ii) (2S, 3S)-3-(2-Phenoxy-5-(trifluoromethyl) benzyl)amino-2-phenylpiperidine dihydrochloride (Compound 7)

To a stirred suspension of Compound 1 (150 mg, 0.60 mmol) and Compound 6 (160 mg, 0.60 mmol) in dry $CH_2Cl_2$ (6 ml) was added NaBH(OAc)$_3$ (179 mg, 0.84 mmol) portionwise under nitrogen at room temperature. The reaction mixture was stirred at room temperature for 3 hr. This was basified with sat. $NaHCO_3$ aq., extracted with $CH_2Cl_2$, dried with $MgSO_4$, and concentrated to give crude (2S, 3S)-3-(2-phenoxy-5-(trifluoromethyl)benzyl)amino-2-phenylpiperidine as a yellow. This was purified with chromatography to give pure (2S, 3S)-3-(2-phenoxy-5-(trifluoromethyl)benzyl)amino-2-phenylpiperidine as a yellow oil (135 mg). This was diluted with ethyl acetate, added HCl-MeOH, and concentrated. The white solid was recrystallized from MeOH-ether to give Compound 7 as a white crystalline (108 mg, 36.0%).

mp 190–197° C.

$^1$H-NMR(CDCl$_3$, free base) 7.39–7.18 (m, 8H), 7.15–7.09 (m, 2H), 6.79–6.71 (m, 3H), 3.90 (d, J=2.2 Hz, 1H), 3.66 (d, J=14.7 Hz, 1H), 3.51 (d, J=14.7 Hz, 1H), 3.28–3.23 (m, 1H), 2.90 (d, J=2.6 Hz, 1H), 2.66 (dt, J=12.1, 2.9 Hz, 1H), 2.11–2.06 (m, 1H), 1.96–1.81 (m, 1H), 1.69–1.56 (m, 1H), 1.46–1.41 (m, 1H)

EXAMPLE 5

Preparation of (2S, 3S)-2-Phenyl-3-(5-(2,2,2-trifluoro-1-(trifluoromethyl)ethyl)-2-methoxybenzyl) aminopiperidine dihydrochloride (Compound 15)

(i) 4-(2,2,2-Trifluoro-1-(trifluoromethyl)ethyl) anisole (Compound 8)

This compound was prepared according to the procedures described in *J. Am. Chem. Soc.*, 820(1972)

(ii) 5-(2,2,2-Trifluoro-1-(trifluoromethyl)ethyl)-2-methoxybenzaldehyde (Compound 9)

To a stirred and ice-cooled solution of Compound 8 (650 mg, 2.5 mmol) in dry $CH_2Cl_2$ (15 ml) was added neat TiCl$_4$ (950 mg, 5.0 mmol) followed by Cl$_2$CHOMe (600 mg, 5.0 mmol). After the addition was complete, the mixture was stirred at room temperature for 5 hr, poured into H$_2$O (60 ml), and extracted with $CH_2Cl_2$. The combined extracts were dried (Na$_2$SO$_4$), and concentrated in vacuo to give a yellow oil, which was purified by a column chromatography on silica gel to give Compound 9 (650 mg, 90%)

$^1$H-NMR (CDCl$_3$) 10.47 (s, 1H), 7.86–7.08 (m, 3H), 4.05 (hep, J=8 Hz, 1H), 3.98 (s, 3H)

(iii) (2S,3S)-3-(2-Methoxybenzyl)amino-2-phenylpiperidine (Compound 10)

This compound was prepared according to the procedures described in WO-93-01170.

(iv) (2S, 3S)-1-tert-Butoxycarbonyl-3-(2-methoxybenzyl)aminopiperidine (Compound 11)

To a stirred and ice-cooled mixture of Compound 10 (10 g, 27 mmol), 3M NaOH aq. (36 ml, 110 mmol) and tert-BuOH (15 ml) was added (tert-BuOCO)$_2$O (7.4 g, 34 mmol). After stirring at room temperature overnight, the mixture was extracted with AcOEt. The combined AcOEt extracts were washed with H$_2$O, and sat. NaCl aq, dried (Na$_2$SO$_4$), and concentrated in vacuo to give Compound 11 (11 g, quant.) as a pale yellow oil.

$^1$H-NMR (CDCl$_3$) 7.58 (br.d, J=7.3 Hz, 2H), 7.36–7.16 (m, 5H), 6.89 (ddd, J=7.5, 7.5, 1.1 Hz, 1H), 6.81 (dd, J=8.4, 0.8 Hz, 1H), 5.47 (br.s, 1H), 3.96 (dm, J=13.4 Hz, 1H), 3.87 (d, J=13.6 Hz, 1H), 3.79 (d, J=13.6 Hz, 1H), 3.70 (s, 3H), 3.10–2.99 (m, 1H), 2.94 (dd, J=12.5, 3.4 Hz, 1H), 1.87–1.74 (m, 2H), 1.74–1.40 (m, 3H), 1.41 (s, 9H) This was employed in the next step without further purification.

(v) (2S, 3S)-3-Amino-1-tert-butoxycarbonyl-2-phenylpiperidine (Compound 12)

A mixture of Compound 11 (11 g), 20% Pd(OH)$_2$/C (3.1 g), and MeOH (90 ml) was stirred under an atmosphere of H$_2$ at room temperature overnight. After an additional amount of 20% Pd(OH)$_2$/C (0.55 g) was added, the stirring was continued under an atmosphere of H$_2$ at room temperature for three days. The catalyst was filtered off by the aid of celite, and washed with MeOH thoroughly. The combined MeOH filtrate and washings were concentrated in vacuo to give crude Compound 9 (8.6 g, quant.).

This was dissolved in EtOH (20 ml), and then a warmed solution of fumaric acid (1.6 g, 13.5 mmol) in EtOH (20 ml) was added in one portion to this solution at room temperature. The crystals precipitated were collected by filtration, washed with ice-chilled EtOH, and dried in vacuo at 50° C. to give (2S, 3S)-3-amino-1-(tert-butoxycarbonyl)-2-phenylpiperidine semifumarate (6.1 g, 68%) as white short needles.

After a suspension of semifumarate (1.2 g, 3.7 mmol) in H$_2$O was ice-cooled, 20% NaOH aq. was added until the mixture became basic. The mixture was then extracted with AcOEt. The combined AcOEt extracts were washed with sat. NaCl aq., dried (Na$_2$SO$_4$), and concentrated in vacuo to give Compound 12 (0.95 g, 93%).

$^1$H-NMR (CDCl$_3$) 7.47–7.39 (m, 2H), 7.37–7.23 (m, 5H), 5.19 (br.d, J=6.2 Hz, 1H), 4.00 (dm, J=13.0 Hz, 1H), 3.25–3.05 (m, 2H), 1.94–1.83 (m, 1H), 1.83–1.56 (m, 4H), 1.36 (s, 9H), 1.32 (br.s, 2H)

(vi) (2S, 3S)-1-tert-Butoxycarbonyl-2-phenyl-3-(5-(2,2,2-trifluoro-1-(trifluoromethyl)ethyl)-2-methoxybenzyl)aminopiperidine (Compound 13)

To a stirred and ice-cooled solution of Compound 12 (100 mg, 0.3 mmol) and Compound 9 (100 mg, 0.3 mmol) in dry $CH_2Cl_2$ (10 ml) was added NaBH(OAc)$_3$ (210 mg, 1 mmol) in one portion. After the mixture was stirred at room temperature for 20 hours. The mixture was poured into NaHCO$_3$ aq., and extracted with $CH_2Cl_2$. The combined extracts were dried (Na$_2$SO$_4$), and concentrated in vacuo to give Compound 13 as a yellow oil (170 mg).

$^1$H-NMR (CDCl$_3$) 7.61–6.82 (m, 8H), 5.45 (br, 1H), 4.08–3.65 (m, 3H), 3.74 (s, 3H), 3.10–2.96 (m, 6H), 1.90–1.20 (m, 4H), 1.39 (s, 9H) This was employed in the next step without further purification.

(vii) (2S, 3S)-2-Phenyl-3-(5-(2,2,2-trifluoro-1-(trifluoromethyl)ethyl)-2-methoxybenzyl) aminopiperidine (Compound 14)

To a solution of Compound 13 (170 mg) in AcOEt (6 ml) was added conc. HCl (1 ml). The mixture was stirred at room temperature for 45 minutes. The mixture was poured into NaHCO₃ aq., and extracted with CH₂Cl₂. The combined extracts were dried (Na₂SO₄), and concentrated in vacuo to give Compound 14 (160 mg) as a yellow oil.

$^1$H-NMR (CDCl₃) 7.36–6.68 (m, 8H), 3.95–3.26 (m, 5H), 3.55 (s, 3H), 2.89–1.40 (m, 6H)

MS 446 (M+) This was employed in the next step without further purification.

(viii) (2S, 3S)-2-Phenyl-3-(5-(2,2,2-trifluoro-1-(trifluoromethyl(ethyl)-2-methoxybenzyl) aminopiperidine dihydrochloride (Compound 15)

To a solution of Compound 14 (160 mg) in CH₂Cl₂ (10 ml) was added an excess amount of 10% HCl-MeOH (6 ml). After the solvent was evaporated in vacuo, the residual solid was recrystallized from IPA to give Compound 15 (130 mg, 83%; three steps) as a colorless crystal.

mp 290–294° C.

EXAMPLE 6

Preparation of (2S, 3)-2-Phenyl-3-(5-(1,2,2,2-tetrafluoro-1-(trifluoromethyl)ethyl)-2-methoxybenzyl)aminopiperidine dihydrochloride (Compound 18)

(i) 4-(1,2,2,2-Tetrafluoro-1-(trifluoromethyl)ethyl) anisole (Compound 16)

This compound was prepared according to the procedures described in Nippon Kagaku Kaishi, 2351(1973).

(ii) 5-(1,2,2,2-Tetrafluoro-1-(trifluoromethyl)ethyl)-2-methoxybenzaldehyde (Compound 17)

This compound was prepared from Compound 16 in the same manner of Compound 9.

$^1$H-NMR (CDCl₃) 10.49 (s, 1H), 8.13–7.12 (m, 3H), 4.02 (s, 3H)

(iii) (2S, 3S)-2-Phenyl-3-(5-(1,2,2,2-tetrafluoro-1-(trifluoromethyl)ethyl)-2-methoxybenzyl) aminopiperidine dihydrochloride (Compound 18)

This compound was prepared from Compound 1 and Compound 17 in the same manner of Compound 2.

mp 265–270° C.

$^1$H-NMR (CDCl₃, free base) 7.44–6.72 (m, 8H), 3.96–2.75 (m, 6H), 3.53 (s, 3H), 2.89–1.40 (m, 4H)

MS (free base) 464 (M+)

EXAMPLE 7

Preparation of (2S, 3s)-3-(5-(1,1-Difluoroethyl)-2-(trifluoromethoxy)benzyl)amino-2-phenylpiperidine dihydrochloride (Compound 28)

(i) 3-Iodo-4-(trifluoromethoxy)benzaldehyde (Compound 19)

Trifluoromethanesulfonic acid (18.6 ml, 0.21 mmol) was added to N-iodosuccinimide (10.4 g, 46.3 mmol) dropwise with ice-cooling under an atmosphere of N₂. To the resultant deep blue mixture was added 4-(trifluoromethoxy) benzaldehyde (4.0 g, 21.0 mmol) dropwise with ice-cooling. After stirring at room temperature for 4 h, the reaction mixture was poured into an ice-water (50 ml). The mixture was extracted with CH₂Cl₂. The combined solution was washed with Na₂S₂O₃ aq., Na₂CO₃ aq. and brine, dried (MgSO₄). treated with activated charcoal, and concentrated in vacuo to give crude Compound 19 (6.56 g, 99%) as a pale orange oil. This solidified spontaneously on standing in a refrigerator (a long needle). This was employed in the next step without further purification.

$^1$H-NMR(CDCl₃) 9.95(s, 1H), 8.39(d, J=1.9 Hz, 1H), 7.91(dd, J=8.5, 1.9 Hz, 1H), 7.41(dq, J=8.5, 1.2 Hz, 1H)

(ii) 3-Cyano-4-(trifluoromethoxy)benzaldehyde (Compound 20)

To a stirred suspension of Compound 19 (6.85 g, 21.7 mmol) and zinc cyanide (4.07 g, 34.7 mmol) in dry DMF (35 ml) was added tetrakis(triphenylphosphine)palladium(0) (3.00 g, 2.60 mmol) portionwise at room temperature. The reaction mixture was heated at 100° C. for 9 h. The reaction mixture was diluted with toluene (100 ml)-2M NH₃ aq. (100 ml). The organic layer was separated. The aqueous layer was diluted with toluene (100 ml), filtered through a pad of celite and the filter cake was washed with toluene. The organic layer was separated and the aqueous layer was extracted with toluene. The combined solution was washed with 2M NH₃ aq. (50 ml) and brine, dried (MgSO₄), and concentrated in vacuo to give crude product as a dark tan oil.

The crude product was purified by column chromatography on silica gel with hexane-ethyl acetate(10:1–5:1) to give Compound 20 (2.87 g, 62%) as a pale yellow oil.

$^1$H-NMR(CDCl₃)10.04(s, 1H), 8.26(d, J=1.4 Hz, 1H), 8.19(dd, J=8.4, 1.4 Hz, 1H), 7.59(dq, J=8.4, 1.8 Hz, 1H)

(iii) 5-(1-Hydroxyethyl)-2-(trifluoromethoxy) benzonitrile (Compound 21)

To a stirred solution of Compound 20 (2.59 g, 12.0 mmol) in dry THF (25 ml) was added MeMgBr (4.42 ml, 13.2 mmol, 3.0 M in diethyl ether solution) with ice-cooling under N₂. The reaction mixture was stirred at 0° C. for 1 h, and then for 2 h at room temperature. The mixture was diluted with sat. NH₄Cl (20 ml) with ice-cooling. The mixture was extracted with ether. The combined solution was washed with brine, dried (MgSO₄), and concentrated in vacuo to give crude Compound 21 (2.78 g, quant.) as a yellow oil. This was employed in the next step without further purification.

$^1$H-NMR(CDCl₃) 7.75(d, J=2.2 Hz, 1H), 7.66(dd, J=8.7, 2.2 Hz, 1H), 7.39(dq, J=8.7, 1.7 Hz, 1H), 5.03–4.90(m, 1H), 2.02(br.s, 1H), 1.51(d, J=6.6 Hz, 3H)

(iv) 3-Cyano-4-(trifluoromethoxy)acetophenone (Compound 22)

To a stirred solution of Compound 21 (2.78 g, 12.0 mmol) in dry CH₂Cl₂ (100 ml) was added manganese(IV)oxide (activated; 13.9 g) portionwise at room temperature. The mixture was refluxed for 2.5 h. After cooling to room temperature, the mixture was filtered through a pad of celite and the catalyst was washed with CH₂Cl₂. The filtrate and washings were concentrated in vacuo to give crude Compound 22 (2.31 g, 84%) as a yellow solid. This was employed in the next step without further purification.

$^1$H-NMR(CDCl₃) 8.66 and 8.31(each d, J=2.2 Hz, total 1H), 8.24 and 8.17(each dd, J=8.8, 2.2 Hz, total 1H), 7.54–7.47 and 7.46–7.39(each m, total 1H), 2.66 and 2.65 (each s, total 3H)

(v) 2-Methyl-2-(3-cyano-4-(trifluoromethoxy) phenyl)-1,3-dithiolane (Compound 23)

To a stirred solution of Compound 22 (2.31 g, 10.1 mmol) in dry CH₂Cl₂(30 ml) was added 1,2-ethanedithiol (1.42 g, 15.1 mmol) and boron trifluoride etherate (1.14 g, 8.1 mmol) at room temperature. The reaction mixture was stirred at room temperature for 15 h. The mixture was diluted with 5% NaOH aq. (40 ml) and the organic layer was separated. The aqueous layer was extracted with $CH_2Cl_2$. The combined solution was washed with brine, dried ($MgSO_4$), and concentrated in vacuo to give crude product as a purple oil. The crude product was purified by column chromatography on silica gel with hexane-ethyl acetate(50:1–20:1) to give Compound 23 (2.61 g, 85%) as a purple oil.

$^1$H-NMR(CDCl$_3$) 8.15(d, J=2.6 Hz, 1H), 8.03(dd, J=8.8, 2.6 Hz, 1H), 7.32(dd, J=8.8, 1.5 Hz, 1H), 3.58–3.44(m, 2H), 3.43–3.28(m, 2H), 2.13(s, 3H).

(vi) 5-(1,1-Difluoroethyl)-2-(trifluoromethoxy) benzonitrile (Compound 24)

To a stirred suspension of 1,3-dibromo-5,5-dimethylhydantoin (DBH)(1.07 g, 3.73 mmol) in dry $CH_2Cl_2$ (8 ml) was added HF-Pyridine (0.95 ml, 4.11 mmol) at −78° C. (acetone-dry ice). To this was added a solution of Compound 23 (570 mg, 1.87 mmol) in dry $CH_2Cl_2$ (4 ml) at same temperature. The reaction mixture was stirred at −78° C. for 10 min, and then for 30 min at room temperature. The mixture was poured into sat. $NaHCO_3$ aq. (40 ml) and stirred at room temperature for 15 min. The mixture was filtered through a pad of celite and the filter cake was washed with ether. The organic layer was separated and the aqueous layer was extracted with ether. The combined solution was washed with 10% HCl aq. and brine, dried ($MgSO_4$), and concentrated in vacuo to give crude product (670 mg). The crude product was purified by prep. TLC with hexane-ethyl acetate(5:1) to give Compound 24 (408 mg, 87%) as a yellow oil.

$^1$H-NMR(CDCl$_3$) 7.88–7.85(m, 1H), 7.83–7.76(m, 1H), 7.51–7.43(m, 1H), 1.94(t, J=18.3 Hz, 3H)

IR(film) 2245, 1619, 1504, 1417, 1391, 1272, 1265, 1212, 1185, 1120, 924, 844.

(vii) 5-(1,1-Difluoroethyl)-2-(trifluoromethoxy) benzaldehyde (Compound 25)

To a stirred solution of Compound 24 (1.31 g, 5.22 mmol) in dry $CH_2Cl_2$(20 ml) was added a solution of diisobutylaluminum hydride(DIBAL) (6.20 ml, 6.26 mmol, 1.01M in toluene solution) with ice-cooling. The reaction mixture was stirred at 0-C. for 3 h. To the mixture was added $H_2O$ (6 ml), followed by 6M HCl aq. (20 ml) and stirred at room temperature for 1.5 h. The organic layer was separated and the aqueous layer was extracted with $CH_2Cl_2$. The combined solution was washed with sat. $NaHCO_3$ aq. and brine, dried($MgSO_4$) and concentrated in vacuo to give crude product. The crude product was purified by column chromatography on silica gel with hexane-ethyl acetate (50:1–30:1) to give Compound 25 (1.17 g, 88%) as a yellow oil.

$^1$H-NMR(CDCl$_3$) 10.39(s, 1H), 8.15–8.08(m, 1H), 7.86–7.78(m, 1H), 7.48–7.40(m, 1H), 1.95(t, J=18.3 Hz, 3H).

IR(film) 1702, 1618, 1499, 1390, 1269, 1212, 1180, 1115, 923.

(viii) (2S, 3S)-1-tert-Butoxycarbonyl-3-(5-( 1,1-difluoroethyl)-2-(trifluoromethoxy)benzyl)amino-2-phenylpiperidine (Compound 26)

To a stirred solution of Compound 12 (500 mg, 1.81 mmol) and Compound 25 (552 mg, 2.17 mmol) in dry $CH_2Cl_2$ (10 ml) was added sodium triacetoxyborohydride (1.15 g, 5.43 mmol) portionwise at room temperature. Then to this was added acetic acid (109 mg, 1.81 mmol) at same temperature. The reaction mixture was stirred at room temperature for 66 h. The reaction mixture was basified to pH10–11 with 10% NaOH aq. with ice-cooling. The organic layer was separated and the aqueous layer was extracted with $CH_2Cl_2$. The combined solution was washed with brine, dried ($MgSO_4$), and concentrated in vacuo to give crude product (1.46 g) as a pale yellow oil. This was employed for the next step without further purification.

(ix) (2S, 3S) -3-(5-(1,1-Difluoroethyl)-2-(trifluoromethoxy)benzyl)amino-2-phenylpiperidine (Compound 27)

To a stirred solution of Compound 26 (660 mg, 1.25 mmol) in ethyl acetate (6 ml) was added c. HCl aq. (2 ml) with ice-cooling. The reaction mixture was stirred at room temperature for 50 min. The mixture was basified to pH10–11 with 10% NaOH aq. with ice-cooling. The organic layer was separated and the aqueous layer was extracted with AcOEt. The combined solution was washed with brine, dried ($MgSO_4$), and concentrated in vacuo to give crude product as a pale yellow oil. The crude product was purified by column chromatography on silica gel with dichloromethane-methanol (20:1) to give Compound 27 (360 mg, 70%) as a yellow oil.

$^1$H-NMR(CDCl$_3$) 7.40–7.30(m, 7H), 7.17–7.10(m, 1H), 3.91(d, J=2.2 Hz, 1H), 3.61(d, J=15.0 Hz, 1H), 3.47(d, J=15.0 Hz, 1H), 3.30–3.20(m, 1H), 2.89–2.73(m, 2H), 2.13–2.00(m, 1H), 1.97–1.71(m, 1H), 1.82(t, J=18.1 Hz, 3H), 1.70–1.55(m, 1H), 1.53–1.40(m, 1H).

IR(film) 3340, 1605, 1497, 1454, 1419, 1387, 1354, 1309, 1259, 1250, 1221, 1173, 1118, 920, 874, 834, 753, 702.

(x) (2S, 3S)-3-(5-(1,1-Difluoroethyl)-2-(trifluoromethoxy)benzyl)amino-2-phenylpiperidine dihydrochloride (Compound 28)

The Compound 27 (360 mg. 0.87 mmol) was treated with methanol-hydrogen chloride (ca 20 ml) and the solvent was evaporated in vacuo to give crude product as a white solid. The crude product was recrystallized from ethanol-diethyl ether to give Compound 28 (370 mg, 87%) as a white solid.

mp: 172–174° C.

IR(KBr) 3435, 1607, 1573, 1512, 1458, 1303, 1264, 1208, 1173, 1124, 924, 906, 826, 747, 698.

EXAMPLE 8

Preparation of (2S, 3S)-3-(5-(1,1-Difluoroethyl)-2-methoxybenzyl)amino-2-phenylpiperidine monomandelate (Compound 37)

(i) 2-Bromo-5-(1-hydroxyethyl)anisole (Compound 29)

This compound was prepared from 3-bromo-4-methoxybenzaldehyde in the same manner of Compound 21.

$^1$H-NMR(CDCl$_3$) 7.57(d, J=2.2 Hz, 1H), 7.28(dd, J=8.4, 2.2 Hz, 1H), 6.88(d, J=8.4 Hz, 1H), 4.84(q, J=6.2 Hz, 1H), 3.89(s, 3H), 1.78(br.s, 1H), 1.47(d, J=6.2 Hz, 3H)

(ii) 3-Bromo-4-methoxyacetophenone (Compound 30)

This compound was prepared from Compound 29 in the same manner of Compound 22.

¹H-NMR(CDCl₃) 8.17(d, J=2.2 Hz, 1H), 7.92(dd, J=8.4, 2.2 Hz, 1H), 6.94(d, J=8.4 Hz, 1H), 3.97(s, 3H), 2.56(s, 3H).

(iii) 3-Cyano-4-methoxyacetophenone (Compound 31)

This compound was prepared from Compound 30 in the same manner of Compound 20.

¹H-NMR(CDCl₃) 8.21–8.14(m, 2H), 7.09–7.01(m, 1H), 4.02(s, 3H), 2.58(s, 3H)

(iv) 2-Methyl-2-(3-cyano-4-methoxyphenyl)-1,3-dithiolane (Compound 32)

This compound was prepared from Compound 31 in the same manner of Compound 23.

¹H-NMR(CDCl₃) 7.98(d, J=2.6 Hz, 1H), 7.93(dd, J=8.8, 2.6 Hz, 1H), 6.91(d, J=8.8 Hz, 1H), 3.93(s, 3H), 3.53–3.32 (m, 4H), 2.11(s, 3H).

(v) 5-(1,1-Difluoroethyl)-2-methoxybenzonitorile (Compound 33)

To a stirred suspension of N-iodosuccinimide(12.5 g, 55.7 mmol) in dry CH₂Cl₂(60 ml) was added HF-Pyridine (6.81 ml, 30.6 mmol) at −78° C. (acetone-dry ice), followed by a solution of Compound 32 (3.50 g, 13.9 mmol) in dry CH₂Cl₂ (10 ml) at same temperature. The reaction mixture was stirred at −78° C. for 10 min, and then for 30 min at −10° C. (methanol-ice). The mixture was poured into sat. NaHCO₃ aq. (100 ml) and stirred at room temperature for 2 h. The mixture was filtered through a pad of celite and the filter cake was washed with CH₂Cl₂. The organic layer was separated and the aqueous layer was extracted with CH₂Cl₂. The combined solution was washed with sat. Na₂S₂O₃ aq., 10% HCl aq. and brine, dried (MgSO₄), and concentrated in vacuo to give crude product as a yellow oil.

The crude product was purified by column chromatography on silica gel with hexane-ethyl acetate(5:1) to give Compound 33(2.67 g, 97%) as a white solid.

¹H-NMR(CDCl₃) 7.73–7.65(m, 2H), 7.02(d, J=8.4 Hz, 1H), 3.97(s, 3H), 1.91(t, J=18.0 Hz, 3H)

(vi) 5-(1,1-Difluoroethyl)-2-methoxybenzaldehyde (Compound 34)

This compound was prepared from Compound 33 in the same manner of Compound 25.

¹H-NMR(CDCl₃) 10.47(s, 1H), 7.97(d, J=2.6 Hz, 1H), 7.72(dd, J=8.8, 2.6 Hz, 1H), 7.05(d, J=8.8 Hz, 1H), 3.97(s, 3H), 1.93(t, J=18.0 Hz, 3H)

(vii) (2S, 3S)-1-tert-Butoxycarbonyl-3-(5-(1,1-Difluoroethyl)-2-methoxybenzyl)amino-2-phenylpiperidine (Compound 35)

This compound was prepared from Compounds 12 and 34 in the same manner of Compound 26. This was employed in the next step without further purification.

(viii) (2S, 3S)-3-(5-(1,1-Difluoroethyl)-2-methoxybenzyl)amino-2-phenylpiperidine (Compound 36)

This compound was prepared from Compound 35 in the same manner of Compound 27

¹H-NMR(CDCl₃) 7.35–7.18(m, 6H), 7.15(d, J=2.2 Hz, 1H), 6.68(d, J=8.4 Hz, 1H), 3.89(d, J=2.2 Hz, 1H), 3.66(d, J=13.9 Hz, 1H), 3.49(s, 3H), 3.41(d, J=13.9 Hz, 1H), 3.32–3.20(m, 1H), 2.86–2.72(m, 2H), 2.18–2.05(m, 1H), 2.02–1.81(m, 1H), 1.86(t, J=18.0 Hz, 3H), 1.72(br.s, 2H), 1.75–1.52(m, 1H), 1.47–1.35(m, 1H).

IR(film) 3335, 1614, 1502, 1451, 1385, 1308, 1280, 1252, 1174, 1123, 1030, 923, 901, 870, 816, 751, 701.

(ix) (2S, 3S)-3-(5-(1,1-Difluoroethyl)-2-methoxybenzyl)amino-2-phenylpiperidine monomandelate (Compound 37)

To a solution of Compound 36 (179 mg, 0.50 mmol) in ethanol (3 ml) was added (R)-(−)-mandelic acid (75.4 mg, 0.50 mmol) at room temperature. After the solvent was evaporated in vacuo, the residue was recrystallized from ethanol-diethyl ether to give Compound 37 (168 mg, 66%) as a white solid.

mp: 177–179° C.

IR(film) 3400, 1615, 1576, 1506, 1473, 1454, 1399, 1384, 1362, 1345, 1318, 1249, 1172, 1137, 1115, 1054, 1028, 900, 756, 742, 698.

EXAMPLE 9

Preparation of (2S, 3S)-3-(2-Methoxy-5-(1,1,2,2,2-pentafluoroethyl)benzyl)amino-2-phenylpiperidine dihydrochloride (Compound 43)

(i) 2-(3-Bromo-6-methoxyphenyl)-1,3-dioxane (Compound 38)

A mixture of 5-bromo-o-anisaldehyde (10.0 g, 46.5 mmol), propane-1,3-diol (3.90 g, 51.2 mmol) and BF₃-Et₂O (0.15 ml) in toluene (50 ml) was refluxed in a Dean-Stark apparatus for 3 h. The reaction mixture was cooled, diluted with ether. The organic layer was washed successively with sat. NaHCO₃ aq., water and brine, dried (MgSO₄), and concentrated in vacuo to give crude product. The residue was distilled to give Compound 38 (10.7 g, 84%) as a colorless oil.

bp: 124–125° C./0.23–0.25 mmHg

¹H-NMR(CDCl₃) 7.74(d, J=2.6 Hz, 1H), 7.39(dd, J=8.8, 2.6 Hz, 1H), 6.74(d, J=8.8 Hz, 1H), 5.81(s, 1H), 4.31–4.17 (m, 2H), 4.06–3.91(m, 2H), 3.82(s, 3H), 2.35–2.10(m, 1H), 1.50–1.35(m, 1H).

(ii) 2-(2-Methoxy-5-(1,1,2,2,2-pentafluoroethyl) phenyl)-1,3-dioxane (Compound 39)

A 50 ml round bottom flask equipped with Dean-Stark trap and reflux condenser was charged with Compound 38 (1.0 g, 3.66 mmol), sodium pentafluoropropionate (1.29 g, 6.95 mmol) and copper(I) iodide (1.46 g, 7.69 mmol), DMF (15 ml)-toluene (6 ml). The slurry was heated to 120–140° C. (bath temperature) and toluene (6 ml) was removed by distillation. The reaction mixture was heated at 140° C. (inner temperature) for 15 h. The mixture was diluted with water (40 ml)-toluene (15 ml)-ethyl acetate (60 ml). The mixture was filtered through a pad of celite and the filter cake was washed with ethyl acetate. The filtrate was washed with water, and brine, dried(MgSO₄) and concentrated in vacuo to give crude product. The crude product was purified by column chromatography on silica gel with hexane-ethyl acetate(10:1–5:1) to give Compound 39 (1.07 g) as a pale yellow oil ¹H-NMR(CDCl₃) 7.87(d, J=2.2 Hz, 1H), 7.53(dd, J=8.8, 2.2 Hz, 1H), 6.96(d, J=8.8 Hz, 1H), 5.85(s, 1H), 4.26(dd, J=11.0, 4.4 Hz, 2H), 4.00(td, J=12.3, 2.2 Hz, 2H), 3.89(s, 3H), 2.36–2.15(m, 1H), 1.50–1.38(m, 1H)

(iii) 2-Methoxy-5-(1,1,2,2,2-pentafluoroethyl) benzaldehyde (Compound 40)

To a stirred solution of Compound 39 (1.0 g) in acetone (30 ml) was added conc. HCl (4 ml) at room temperature. The reaction mixture was stirred at room temperature for 5 h. The solvent was evaporated in vacuo and the residue was extracted with ether. The combined solution was washed with sat. NaHCO$_3$ aq., and brine, dried(MgSO$_4$) and concentrated in vacuo to give crude product (790 mg) as a yellow solid. The crude product was purified by column chromatography on silica gel with hexane-isopropyl ether (10:1–3:1) to give Compound 40 (275 mg) as a pale yellow solid.

1H-NMR(CDCl$_3$) 10.48(s, 1H), 8.08(d, J=2.2 Hz, 1H), 7.77(dd, J=8.8, 2.2 Hz, 1H), 7.13(d, J=8.8 Hz, 1H), 4.02(s, 3H)

(iv) (2S, 3S)-1-tert-Butoxycarbonyl-3-(2-Methoxy-5-(1,1,2,2,2-pentafluoroethyl)benzyl)amino-2-phenylpiperidine (Compound 41)

This Compound was prepared from Compound 12 and Compound 40 in the same manner of Compound 26. This was employed in the next step without further purification.

(v) (2S, 3S)-3-(2-Methoxy-5-(1,1,2,2,2-pentafluoroethyl)benzyl)amino-2-phenylpiperidine (Compound 42)

This compound was prepared from Compound 41 in the same manner of Compound 27.

$^1$H-NMR(CDCl$_3$) 7.38(dd, J=8.4, 2.2 Hz, 1H), 7.34–7.18 (m, 6H), 6.74(d, J=8.4 Hz, 1H), 3.90(d, J=2.2 Hz, 1H), 3.69(d, J=14.3 Hz, 1H), 3.53(s, 3H), 3.40(d, J=14.3 Hz, 1H), 3.34–3.24(m, 1H), 2.88–2.74(m, 2H), 2.15–1.83(m, 4H), 1.69–1.53(m, 1H), 1.50–1.38(m, 1H)

IR(film) 3330, 1614, 1501, 1460, 1334, 1304, 1275, 1258, 1203, 1145, 1119, 1096, 1029, 1004, 870, 815, 746, 700.

(vi) (2S, 3S-3-(2-Methoxy-5-(1,1.2,2,2-pentafluoroethyl)benzyl)amino-2-phenylpiperidine dihydrochloride (Compound 43)

This compound was prepared from Compound 42 in the same manner of Compound 28.

mp : 201–202° C.

IR(KBr) 3455, 1617, 1554, 1506, 1453, 1443, 1416, 1337, 1282, 1258, 1221, 1202, 1180, 1148, 1131, 1091, 1010, 744, 693.

EXAMPLE 10

Preparation of (2S, 3S)-3-(2-Methoxy-5-(2,2,2-trifluoroethyl)benzyl)amino-2-phenylpiperidine dihydrochloride (Compound 49)

(i) 1-(4-Methoxyphenyl)-2,2,2-trifluoroethyl bromide (Compound 44)

This compound was prepared according to the procedure described in *J. Am. Chem. Soc.* 111, 1455 (1989)

(ii) 1-(4-Methoxyphenyl)-2,2,2-trifluoroethane (Compound 45)

A solution of Compound 44 (1.08 g, 4.00 mmol) in ethanol (20 ml) was hydrogenated over 10% Pd-C (800 mg) at atmospheric pressure for 16 h. The catalyst was filtered through a pad of celite and the filter cake was washed with CH$_2$Cl$_2$. The combined solution was washed with half-brine and brine, dried (MgSO$_4$), and concentrated in vacuo to give crude Compound 45 ( 760 mg, quant.) as a pale yellow oil.

$^1$H-NMR(CDCl$_3$) 7.24–7.17(m, 2H), 6.93–6.84(m, 2H), 3.81(s, 3H), 3.30(q, J=10.9 Hz, 2H)

(iii) 2-Methoxy-5-(2,2,2-trifluoroethyl)benzaldehyde (Compound 46)

To a stirred solution of Compound 45 (760 mg, 4.00 mmol) in dry CH$_2$Cl$_2$ (15 ml) was added TiCl$_4$ (1.67 g, 8.80 mmol) via a syringe with ice-cooling. After 15 min, to this was added a solution of dichloromethyl methyl ether (920 mg, 8.00 mmol) in dry CH$_2$Cl$_2$ (5 ml) at same temperature. The reaction mixture was stirred at 0 C. for 15 min, and then for 1.5 h at room temperature. The mixture was diluted with water (20 ml) with ice-cooling and stirred at room temperature for 15 min. The organic layer was separated and the aqueous layer was extracted with CH$_2$Cl$_2$. The combined solution was washed with sat. NaHCO$_3$ aq. and brine, dried (MgSO$_4$), and concentrated in vacuo to give crude product as a yellow oil. The crude product was purified by column chromatography on silica gel with hexane-ethyl acetate (40:1–20:1) to give Compound 46 (500 mg, 57%) as a colorless solid(needle).

$^1$H-NMR(CDCl$_3$) 10.46(s, 1H), 7.76(d, J=2.2 Hz, 1H), 7.49(dd, J=8.8, 2.2 Hz, 1H), 7.00(d, J=8.8 Hz, 1H), 3.95(s, 3H), 3.34(q, J=10.6 Hz, 2H).

(iv)(2S,3S)-1-tert-Butoxycarbonyl-3-(2-methoxy-5-(2,2,2-trifluoroethyl)benzyl)amino-2-phenylpiperidine (Compound 47)

This compound was prepared from Compound 12 and Compound 46 in the same manner of Compound 26. This was employed in the next step without further purification.

(v) (2S, 3S)-3-(2-Methoxy-5-(2,2,2-trifluoroethyl) benzyl)amino-2-phenylpiperidine (Compound 48)

This compound was prepared from Compound 47 in the same manner of Compound 27.

$^1$H-NMR(CDCl$_3$) 7.35–7.20(m, 5H), 7.06(dd, J=8.4, 1.8 Hz, 1H), 6.84(d, J=1.8 Hz, 1H), 6.65(d, J=8.4 Hz, 1H), 3.90(d, J=2.2 Hz, 1H), 3.68(d, J=14.3 Hz, 1H), 3.49(s, 3H), 3.42(d, J=14.3 Hz, 1H), 3.35–3.24(m, 1H), 3.20(q, J=11.0 Hz, 2H), 2.88–2.73(m, 2H), 2.20–1.85(m, 4H), 1.68–1.52 (m, 1H), 1.50–1.37(m 1H).

IR(film) 3450, 1614, 1500, 1465, 1445, 1430, 1359, 1328, 1263, 1249, 1237, 1128, 1103, 1074, 1031, 854, 822, 810, 773, 746, 700, 672.

(vi) (2S, 3S)-3-(2-Methoxy-5-(2,2,2-trifluoroethyl) benzyl)amino-2-phenylpiperidine dihydrochloride (Compound 49)

This compound was prepared from Compound 48 in the same manner of Compound 28.

mp : 209–210° C.

IR(KBr) 3450, 1552, 1506, 1451, 1441, 1415, 1369, 1333, 1260, 1241, 1170, 1132, 1086, 1030, 978, 807, 748, 693.

EXAMPLE 11

Preparation of (2S, 3S)-3-(2-Methoxy-5-(1-(trifluoromethyl)ethyl)benzyl)amino-2-phenylpiperidine dihydrochloride (Compound 55)

(i) 1-(4-Methoxyphenyl)-1-(trifluoromethyl)ethyl bromide(Compound 50)

This compound was prepared according to the procedure (J. Am. Chem. Soc., 104, 211 (1982))

(ii) 1-(4-Methoxyphenyl)-1-(trifluoromethyl)ethane (Compound 51)

This compound was prepared from Compound 50 in the same manner of Compound 45.

$^1$H-NMR(CDCl$_3$) 7.28–7.19(m, 2H), 6.93–6.84(m, 2H), 3.81(s, 3H), 3.48–3.27(m, 1H), 1.48(d, J=7.0 Hz, 3H).

(iii) 2-Methoxy-5-(1-(trifluoromethyl)ethyl)benzaldehyde(Compound 52)

This compound was prepared from Compound 51 in the same manner of Compound 46.

$^1$H-NMR(CDCl$_3$) 10.46(s, 1H), 7.79(d, J=2.6 Hz, 1H), 7.52(dd, J=8.8, 2.6 Hz, 1H), 7.00(d, J=8.8 Hz, 1H), 3.94(s, 3H), 3.53–3.32(m, 1H), 1.50(d, J=7.3 Hz, 3H).

(iv) (2S, 3S)-1-tert-Butoxycarbonyl-3-(2-Methoxy-5-(1-(trifluoromethyl)ethyl)benzyl)amino-2-phenylpiperidine(Compound 53)

This compound was prepared from Compounds 12 and 52 in the same manner of Compound 26. This was employed in the next step without further purification.

(v) (2S, 3S)-3-(2-Methoxy-5-(1-(trifluoromethyl)ethyl)benzyl)amino-2-phenylpiperidine(Compound 54)

This compound was prepared from Compound 53 in the same manner of Compound 27.

$^1$H-NMR(CDCl$_3$) 7.35–7.19(m, 5H), 7.13–7.05(m, 1H), 6.91–6.86(m, 1H), 6.68–6.61(m, 1H), 3.91(d, J=2.2 Hz, 1H), 3.75–3.15(m, 7H), 2.88–2.73(m, 2H), 2.30–1.85(m, 4H), 1.70–1.51(m, 1H), 1.50–1.35(m, 1H), 1.42(d, J=7.3 Hz, 3H).

IR(film) 3330, 1612, 1500, 1462, 1385, 1349, 1331, 1295, 1250, 1171, 1157, 1122, 1082, 1049, 1031, 995, 805, 747, 701.

(vi)(2S,3S)-3-(2-Methoxy-5-(1-(trifluoromethyl)ethyl)benzyl)amino-2-phenylpiperidine dihydrochloride (Compound 55)

This compound was prepared from Compound 54 in the same manner of Compound 28.

mp : 217–218° C.

IR(KBr) 3450, 1554, 1505, 1465, 1453, 1442, 1417, 1334, 1253, 1169, 1159, 1144, 1120, 1083, 1050, 1030, 748, 693.

EXAMPLE 12

Preparation of(2S, 3S)-3-[5-(1,1-dimethyl-4,4,4-trifluoro-2-butynyl)-2-methoxybenzyl]amino-2-phenylpiperidine dihydrochloride (Compound 60)

4-(1,1-Dimethyl-2-propynyl)anisole (Compound 56)

This compound was prepared according to the procedures described in *Tetrahedron Lett.*, 4163 (1977).

(ii) 4-(1,1-Dimethyl-4,4,4-trifluoro-2-butynyl)anisole (Compound 57)

To a stirred solution of Compound 56 (0.22 g, 1.26 mmol) in THF (8 ml) was added n-BuLi (1.69 M in hexane, 0.82 ml, 1.39 mmol) at −78° C. under N$_2$, then warmed up to 0° C., and stirred for 1 h. S-(Trifluoromethyl)dibenzothiophenium trifluoromethane-sulfonate (1.01 g, 2.52 mmol) was added, and stirred for 3 h at 0° C. The mixture was quenched by the addition of NaHCO$_3$ aq., and extracted with CH$_2$Cl$_2$. The combined organic layers were dried over MgSO$_4$, filtered, and concentrated. This was purified by SiO$_2$ chromatography to give Compound 57 (38 mg, 13%) as a colorless oil.

$^1$H-NMR (CDCl$_3$) 7.37 (d, 2H, J=8.8 Hz), 6.88 (d, 2H, J=8.8 Hz), 3.80 (s, 3H), 1.62 (s, 6H).

(iii) 5-(1,1-Dimethyl-4,4,4-trifluoro-2-butynyl)-2-methoxybenzaldehyde (Compound 58)

This compound was prepared from Compound 57 in the same manner of Compound 9.

$^1$H-NMR (CDCl$_3$) 10.47 (s, 1H), 7.87 (d, 1H, J=2.9 Hz), 7.71 (dd, 1H, J=8.8, 2.9 Hz), 7.01 (d, 1H, J=8.8 Hz), 3.94 (s, 3H), 1.64 (s, 6H).

(iv) (2S, 3S)-1-tert-Butoxycarbonyl-3-[5-(1,1-dimethyl-4,4,4-trifluoro-2-butynyl)-2-methoxybenzyl]amino-2-phenylpiperidine (Compound 59)

This compound was prepared from Compound 58 and Compound 12 in the same manner of Compound 13.

$^1$H-NMR(CDCl$_3$) 7.62–7.53 (m, 2H), 7.36–7.20 (m, 5H), 6.78 (d, 1H, J=9.2 Hz), 5.53–5.42 (m, 1H), 4.01–3.88 (m, 1H), 3.83 (s, 2H), 3.70 (s, 3H), 3.13–2.93 (m, 2H), 1.92–1.35 (m, 4H), 1.60 (s, 3H), 1.59 (s, 3H), 1.40 (s, 9H).

(v) (2S, 3S)-3-[5-(1,1-Dimethyl-4,4,4-trifluoro-2-butynyl)-2-methoxybenzyl]amino-2-phenylpiperidine dihydrochloride (Compound 60)

To a solution of Compound 59 (34 mg, 0.064 mmol) in AcOEt (8 ml) was added an excess amount of HCl-MeOH. The mixture was stirred for 18 h and then evaporated in vacuo, the residual solid was recrystallized from MeOH-Et$_2$O to give Compound 60 (24 mg, 75%) as a white solid.

mp 225–227° C.

IR(KBr) 3440, 2980, 2935, 2350, 2275, 1558, 1504, 1455, 1416, 1293, 1130 cm$^{-1}$.

$^1$H-NMR (free base; CDCl$_3$) 7.38–7.25 (m, 6H), 7.10 (d, 1H, J=2.6 Hz), 6.67 (d, 1H, J=8.4 Hz), 4.04–4.01 (m, 1H), 3.78 (d, 1H, J=13.9 Hz), 3.53–3.38 (m, 2H), 3.45 (s, 3H), 2.96–2.83 (m, 2H), 2.30–1.60 (m, 4H), 1.58 (s, 6H).

Anal. Calc for C$_{25}$H$_{29}$F$_3$N$_2$O.2HCl: C, 59.65%; H, 6.21%; N, 5.56%. Found: C, 59.38%; H, 6.27%; N, 5.55%.

EXAMPLE 13

Preparation of (2S, 3S)-3-[(5-Methoxy-1-(trifluoromethyl)indan-6-yl)methylamino]-2-phenylpiperidine dihydrochloride (Compound 61)

(i) 1-Hydroxy-5-methoxy-1-(trifluoromethyl)indan (Compound 62)

To a stirred solution of 5-methoxy-1-indanone (1.00 g, 6.17 mmol) and trifluoromethyltrimethylsilane (1.32 g, 9.26 mmol) in dry THF (15 ml) was added 1.0M THF solution of tetrabutylammonium fluoride (0.05 ml) with ice-cooling.The reaction mixture was stirred at room temperature for 21 h. To a mixture was 1N HCl (20 ml). and stirred at room temperature for 25 h. The reaction mixture was diluted with CH$_2$Cl$_2$-water. The organic layer was separated and the aqueous layer was extracted with CH$_2$Cl$_2$. The combined solution was washed with water and brine, dried (MgSO$_4$) and concentrated in vacuo to give crude product as a dark yellow oil. The crude product was purified by column chromatography on silica gel with hexane-ethyl acetate (5:1–3:1) to give Compound 62 (1.05 g, 73%) as a yellow oil.

¹H-NMR (CDCl₃) 7.39 (d, J=8.4 Hz, 1H), 6.88–6.75 (m, 2H), 3.81 (s, 3H), 3.17–2.86 (m, 2H), 2.74–2.57 (m, 1H), 2.43–2.34 (m, 1H), 2.32–2.15 (m, 1H).

(ii) 6-Methoxy-3-(trifluoromethyl)indene (Compound 63)

To a stirred Compound 62(850 mg, 3.66 mmol) was added PBr₃(9.90 g, 36.6 mmol) with ice-cooling. The reaction mixture was stirred at 80° C. for 6 h. The mixture was diluted with water with ice-cooling and extracted with CH₂Cl₂. The combined solution was washed with sat. NaHCO₃ and brine, dried(MgSO₄) and concentrated in vacuo to give crude product as a yellow oil. The crude product was purified by column chromatography on silica gel with hexane-ethyl acetate(50:1–40:1) to give Compound 63(727 mg, 93%) as a yellow oil.

¹H-NMR(CDCl₃) 7.46–7.38(m, 1H), 7.10–7.05(m, 1H), 6.90(dd, J=8,4, 2.6 Hz, 1H), 6.87–6.81(m, 1H), 3.84(s, 3H),3.50–3.47(m, 2H).

(iii) 5-Methoxy-1-(trifluoromethyl)indan (Compound 64)

A solution of Compound 63 (180 mg, 0.84 mmol) in ethanol (5 ml) was hydrogenated over 10% Pd-C (90 mg) at atmospheric pressure for 4.5 h. The catalyst was filtered through a pad of celite and the filter cake was washed with CH₂Cl₂. The combined solution was washed with half-brine and brine, dried (MgSO₄), and concentrated in vacuo to give crude Compound 64 (147 mg, 81%) as a pale yellow oil.

¹H-NMR(CDCl₃) 7.36–7.20(m, 1H), 6.88–6.69(m, 2H), 3.90–3.62(m, 4H), 3.20–2.80(m, 2H), 2.48–2.19(m, 2H).

(iv) 6-Formyl-5-methoxy-1-(trifluoromethyl)indan (Compound 65)

This compound was prepared from Compound 64 in the same manner of Compound 46.

¹H-NMR(CDCl₃) 10.41(s, 1H), 7.85(s, 1H), 6.90(s, 1H), 3.93(s, 3H), 3.90–3.70(m, 1H), 3.24–2.87(m, 2H), 2.50–2.20(m, 2H).

(v) (2S, 3S)-1-tert-Butoxycarbonyl-3-[(5-methoxy-1-(trifluoromethyl)indan-6-yl)methylamino]-2-phenylpiperidine (Compound 66)

This compound was prepared from Compounds 12 and 65 in the same manner of Compound 26. This was employed in the next step without further purification.

(vi) (2S, 3S)-3-[(5-Methoxy-1-(trifluoromethyl) indan-6-yl)methylamino]-2-phenylpiperidine (Compound 67)

This Compound was prepared from Compound 66 in the same manner of Compound 27.

¹H-NMR(CDCl₃) 7.37–7.17(m, 5H), 6.99(br.s, 1H), 6.58 and 6.56(each s, total 1H), 3.91(d, J=2.2 Hz, 1H), 3.82–3.60 (m, 2H), 3.44(s, 3H), 3.39(d, J=13.9 Hz, 1H), 3.39–3.24(m, 1H), 3.10–2.72(m, 4H), 2.56(br.s, 2H), 2.43–1.85(m, 4H), 1.71–1.35(m, 2H).

(vii) (2S, 3S)-3-[(5-Methoxy-1-(trifluoromethyl) indan-6-yl)methylamino]-2-phenylpiperidine dihydrochloride (Compound 61)

This compound was prepared from Compound 67 in the same manner of Compound 28.

mp: 213–214° C.

IR(KBr) 3435, 1623, 1579, 1560, 1498, 1464, 1452 1434, 1421, 1368, 1297, 1271, 1170, 1138, 1103,1034, 749, 694.

EXAMPLE 14

Preparation of (2S, 3S)-3-[5-(1-Dimethyl-2,2,2-trifluoroethyl)-2-methoxybenzylamino]-2-phenylpiperidine dihydrochloride (Compound 68)

(i) 4-(1-Chloro-1-methyl-2,2,2-trifluoroethyl)anisole (Compound 69)

This compound was prepared according to the procedure described in JP62234034

(ii) 4-(1,1-Dimethyl-2,2,2-trifluoroethyl)anisole (Compound 70)

To a stirred solution of TiCl₄ (57 mg, 0.30 mmol) in dry CH₂Cl₂ (5 ml) was added a solution (1.05 mol/l) of ZnMe₂ (0.87 ml, 0.91 mmol) in toluene via a syringe at −78° C. After 15 min, to this was added a solution of Compound 69 (217 mg, 0.91 mmol) in dry CH₂Cl₂ (2 ml) at same temperature. The reaction mixture was stirred at −78° C. for 1 h and warmed to room temperature. After 2 h, the mixture was diluted with water and stirred for 10 min. The organic layer was separated and the aqueous layer was extracted with CH₂Cl₂. The combined solution was washed with brine, dried(MgSO₄) and concentrated in vacuo to give crude product (200 mg) (Compounds 69:70=1:2.4) as a pale yellow oil. This was employed in the next step without further purification.

(iii) 5-(1,1-Dimethyl-2,2,2-trifluoroethyl)-2-methoxybenzaldehyde (71)

This compound was prepared from mixture of Compounds 69 and 70 in the same manner of Compound 46.

The crude compound was purified by prep. TLC with hexane-ethyl acetate (6:1) to give Compound 71 (75 mg) as a pale yellow oil.

¹H-NMR(CDCl₃) 10.47(s, 1H), 7.95(d, J=2.6 Hz, 1H), 7.74–7.64(m, 1H), 6.99(d, J=8.8 Hz, 1H), 3.94(s, 3H), 1.57(s, 6H).

(iv) (2S, 3S)-1-tert-Butoxycarbonyl-3-[5-(1,1-Dimethyl-2,2,2-trifluoroethyl)-2-methoxybenzylamino]-2-phenylpiperidine (Compound 72)

This compound was prepared from Compound 12 and Compound 71 in the same manner of Compound 26.

This was employed in the next step without further purification.

(v) (2S, 3S)-3-[5-(1,1-Dimethyl-2,2,2-trifluoroethyl)-2-methoxybenzylamino]-2-phenylpiperidine (Compound 73)

This compound was prepared from Compound 72 in the same manner of Compound 27.

¹H-NMR(CDCl₃) 7.35–7.16(m, 6H), 7.15–7.08(m, 1H), 6.65(d, J=8.8 Hz, 1H), 3.91(d, J=2.2 Hz, 1H), 3.69(d, J=13.9 Hz, 1H), 3.48(s, 3H), 3.41(d, J=13.9 Hz, 1H), 3.36–3.22(m, 1H), 2.90–2.71(m, 2H), 2.44(br.s, 2H), 2.20–1.85(m, 2H), 1.70–1.35(m, 2H), 1.49(s, 6H).

(vi) (2S, 3S)-3-[5-(1,1-Dimethyl-2,2,2-trifluoroethyl)-2-methoxybenzylamino]-2-phenylpiperidine dihydrochloride (Compound 68)

This compound was prepared from Compound 73 in the same manner of Compound 28.

mp: 220–221° C.

IR(KBr) 3425, 1564, 1511, 1469, 1453, 1442, 1420 1400, 1290, 1255 1187, 1174, 1131, 1101, 1027, 749, 691.

EXAMPLE 15

Preparation of (2S, 3S)-2-Phenyl-3-(5-(2,2,2-trifluoro-1-methyl-1-(trifluoromethyl)ethyl)-2-methoxybenzyl)aminopiperidine dihydrochloride (Compound 78)

(i) 4-(2,2-Difluoro-1-(trifluoromethyl)ethenyl) anisole (Compound 74)

This compound was prepared according to the procedures described in *J. Am. Chem. Soc.*, 820(1972)

(ii) 4-(2,2,2-Trifluoro-1-methyl-1-(trifluoromethylethyl)anisole (Compound 75)

A mixture of Compound 74 (570 mg, 2.4 mmol), MeI (430 mg, 3.0 mmol), and CsF (760 mg, 5.0 mmol) in DMF (4 ml) was stirred at 80° C. for 3 days. The mixture was diluted with $H_2O$. The organic layer was separated and the aqueous layer was extracted with $CH_2Cl_2$. The combined solution was dried ($Na_2SO_4$) and concentrated in vacuo to give crude product, which was purified by column chromatography on silica gel to give Compound 75 (70 mg, 10%) as a yellow oil.

$^1$H-NMR (CDCl$_3$) 7.53–6.90 (m, 4H), 4.85 (s, 3H), 3.50–3.42 (m, 3H)

(iii) 5-(2,2,2-Trifluoro-1-methyl-1-(trifluoromethyl)ethyl)-2-methoxybenzaldehyde (Compound 76)

This compound was prepared from Compound 75 in the same manner of Compound 9.

$^1$H-NMR (CDCl$_3$) 10.49 (s, 1H), 8.09–7.08 (m, 3H), 4.02 (s, 3H), 3.51–3.45 (m, 3H)

(iv) (2S, 3S)-1-tert-Butoxycarbonyl-2-phenyl-3-(5-(2,2,2-trifluoro-1-methyl-1-(trifluoromethyl)ethyl)-2-methoxybenzylaminopiperidine (Compound 77)

This compound was prepared from Compound 12 and Compound 76 in the same manner of Compound 26.

This was employed in the next step without further purification.

$^1$H-NMR (CDCl$_3$) 7.62–6.86 (m, 8H), 4.06–2.95 (m, 9H), 3.78 (s, 3H), 1.91–1.30 (m, 4H), 1.35 (s, 9H)

(v) (2S, 3S)-2-Phenyl-3-(5-(2,2,2-trifluoro-1-methyl-1-(trifluoromethyl)ethyl-2-methoxybenzyl) aminopiperidine dihydrochloride (Compound 78)

This compound was prepared from Compound 77 in the same manner of Compound 60.

mp 267–270° C.

EXAMPLE 16

Preparation of (2S, 3S)-3-[5-[2,2-Difluoro-1-(trifluoromethyl)ethenyl]-2-methoxy benzyl]amino-2-phenylpiperidine dihydrochloride (Compound 81)

(i) 5-[2,2-Difluoro-1-(trifluoromethyl)ethenyl]-2-methoxybenzaldehyde (Compound 79)

This compound was prepared from Compound 74 in the same manner of Compound 9.

$^1$H-NMR(CDCl$_3$) 10.47 (s, 1H), 7.81 (d, 1H, J=2.2 Hz), 7.51 (dd, 1H, J=8.4, 2.2 Hz), 7.06 (d, 1H, J=8.4 Hz), 3.98 (s, 3H).

(ii) (2S, 3S)-1-tert-Butoxycarbonyl-3-[5-[2,2-difluoro-1-(trifluoromethyl)ethenyl]-2-methoxybenzyl]amino-2-phenylpiperidine (Compound 80)

This compound was prepared from Compound 79 and Compound 12 in the same manner of Compound 13.

$^1$H-NMR (CDCl$_3$) 7.63–7.55 (m, 2H), 7.37–7.15 (m, 5H), 6.83 (d, 1H, J=8.4 Hz), 5.53–5.42 (m, 1H), 4.02–3.92 (m, 1H), 3.83 (s, 2H), 3.74 (s, 3H), 3.12–2.94 (m, 2H), 1.94–1.40 (m, 4H), 1.40 (s, 9H).

(iii) (2S, 3S)-3-[5-[2,2-Difluoro-1-(trifluoromethyl)ethenyl]-2-methoxybenzyl]amino-2-phenylpiperidine dihydrochloride (Compound 81)

This compound was prepared from Compound 80 in the same manner of Compound 60.

mp 235–237° C.

$^1$H-NMR (free base; CDCl$_3$) 7.35–7.18 (m, 5H), 7.15–7.07 (m, 1H), 6.89–6.86 (m, 1H), 6.70 (d, 1H, J=8.4 Hz), 3.91 (d, 1H, J=2.6 Hz), 3.69 (d, 1H, J=14.7 Hz), 3.53 (s, 3H), 3.42 (d, 1H, J=14.7 Hz), 3.36–3.24 (m, 1H), 2.88–2.75 (m, 2H), 2.18–1.40 (m, 4H).

EXAMPLE 17

Preparation of (2S, 3S)-3-(2,4-Dimethoxy-5-(2,2,2-trifluoroethyl)benzyl)amino-2-phenylpiperidine dihydrochloride (Compound 87)

(i) 1-(2,4-Dimethoxyphenyl)-2,2,2-trifluoroethanol (Compound 82)

This compound was prepared from 2,4-dimethoxybenzaldehyde in the same manner of Compound 62.

$^1$H-NMR(CDCl$_3$) 7.32–6.48(m, 3H), 5.21(quin, J=7 Hz, 1H), 3.85(s, 3H), 3.82(s, 3H), 3.42(d, J=8 Hz, 1H).

(ii) 1-(2,4-Dimethoxyphenyl)-2,2,2-trifluoroethyl bromide (Compound 83)

This compound was prepared from Compound 82 in the same manner of Compound 44.

$^1$H-NMR(CDCl$_3$) 7.58–6.42(m, 3H), 5.81(q, J=11 Hz, 1H), 3.88(s, 3H), 3.86(s, 3H).

(iii) 1-(2,4-Dimethoxyphenyl)-2,2,2-trifluoroethane (Compound 84)

This compound was prepared from Compound 83 in the same manner of Compound 45.

$^1$H-NMR(CDCl$_3$) 7.20–6.45(m, 3H), 3.82(s, 3H), 3.81(s, 3H), 3.37(q, J=11 Hz, 2H).

(iv) 2,4-Dimethoxy-5-(2,2,2-trifluoroethyl) benzaldehyde (Compound 85)

This compound was prepared from Compound 84 in the same manner of Compound 46.

$^1$H-NMR(CDCl$_3$) 10.20(s, 1H), 7.77(s, 1H), 6.46(s, 1H), 3.95(s, 3H), 3.94(s, 3H), 3.38(q, J=11 Hz, 2H).

(v) (2S, 3S)-1-tert-Butoxycarbonyl-3-(2,4-dimethoxy-5-(2,2,2-trifluoroethyl)benzyl)amino-2-phenylpiperidine (Compound 86)

This compound was prepared from Compound 12 and Compound 85 in the same manner of Compound 13.

This was employed in the next step without further purification.

¹H-NMR(CDCl₃) 7.62–7.20(m, 5H), 7.04(s, 1H), 6.42(s, 1H), 4.00–2.92(m, 8H), 3.83(s, 3H), 3.71(s, 3H), 1.90–1.30 (m, 4H), 1.39(s, 9H).

(vi)(2S,3S)-3-(2,4-Dimethoxy-5-(2,2,2-trifluoroethyl)benzyl)amino-2-phenylpiperidine dihydrochloride (Compound 87)

This compound was prepared from Compound 86 in the same manner of Compound 60.

¹H-NMR(free base; CDCl₃) 7.40–7.00(m, 5H), 6.80(s, 1H), 6.27(s, 1H), 3.90–2.72(m, 8H), 3.80(s, 3H), 3.49(s, 3H), 2.15–1.20(m, 4H).

EXAMPLE 18

Preparation of (2S, 3S)-3-((6-Methoxy-1-(trifluoromethyl)-1,2,3,4-tetrahydronaphthalen-7-yl) methyl)amino-2-phenylpiperidine dihydrochloride (Compound 94)

(i) 1-Hydroxy-6-methoxy-1-(trifluoromethyl)-1,2,3, 4-tetrahydronaphthalene(Compound 88)

This compound was prepared from 6-methoxy-1-tetralone in the same manner of Compound 62.

¹H-NMR(CDCl₃) 7.61(d, J=8.8 Hz, 1H), 6.80(dd, J=8.8, 2.6 Hz, 1H), 6.66(d, J=2.6 Hz, 1H), 3.80(s, 3H), 2.90–2.66 (m, 2H), 2.30(s, 1H), 2.40–1.75(m, 4H).

(ii) 6-Methoxy-1-(trifluoromethyl)-3,4-dihydronaphthalene(Compound 89)

This compound was prepared from Compound 88 in the same manner of Compound 63.

¹H-NMR(CDCl₃) 7.39–7.28(m, 1H), 6.80–6.70(m, 2H), 6.61–6.52(m, 1H), 3.81(s, 3H), 2.84–2.72(m, 2H), 2.46–2.30(m, 2H).

(iii) 6-Methoxy-1-(trifluoromethyl)-1,2,3,4-tetrahydronaphthalene (Compound 90)

This compound was prepared from Compound 89 in the same manner of Compound 64.

¹H-NMR(CDCl₃) 7.26(d, J=8.4 Hz, 1H), 6.74(dd, J=8.4, 2.9 Hz, 1H), 6.66(d, J=2.9 Hz, 1H), 3.79(s, 3H), 3.57–3.36 (m, 1H), 2.90–2.62(m, 2H), 2.20–1.60(m, 4H).

(iv) 7-Formyl-6-methoxy-1-(trifluoromethyl)-1,2,3, 4-tetrahydronaphthalene (Compound 91)

This compound was prepared from Compound 90 in the same manner of Compound 46.

¹H-NMR(CDCl₃) 10.39(s, 1H), 7.81(s, 1H), 6.74(s, 1H), 3.91(s, 3H), 3.60–3.40(m, 1H), 2.98–2.70(m, 2H), 2.27–1.65(m, 4H).

(v) (2S, 3S)-1-tert-Butoxycarbonyl-3-((6-methoxy-1-(trifluoromethyl)-1,2,3,4-tetrahydronaphthalen-7-yl)methyl)amino-2-phenylpiperidine (Compound 92)

This compound was prepared from Compounds 12 and 91 in the same manner of Compound 26. This was employed in the next step without further purification.

(vi) (2S, 3S)-3-((6-Methoxy-1-(trifluoromethyl)-1,2, 3,4-tetrahydronaphthalen-7-yl)methyl)amino-2-phenylpiperidine (Compound 93)

This compound was prepared from Compound 92 in the same manner of Compound 27.

¹H-NMR(CDCl₃) 7.38–7.17(m, 5H), 6.94(s, 1H), 6.42 and 6.39(each s, total 1H), 3.90(d, J=1.5 Hz, 1H), 3.73–3.58 (m, 1H), 3.50–3.23(m, 6H), 2.90–2.60(m, 4H), 2.39(br.s, 2H), 2.20–1.52(m, 7H), 1.50–1.34(m, 1H).

(vii) (2S, 3S)-3-((6-Methoxy-1-(trifluoromethyl)-1, 2,3,4-tetrahydronaphthalen-7-yl)methyl)amino-2-phenylpiperidine dihydrochloride (Compound 94)

This compound was prepared from Compound 93 in the same manner of Compound 28.

mp: 227–230° C.

IR(KBr) 3435, 1624, 1587, 1561, 1507, 1466, 1452, 1433, 1420, 1336, 1260, 1247, 1171, 1138, 1116, 1106, 1044, 979, 834, 748, 693.

EXAMPLE 19

Preparation of (2S, 3S)-3-((2,2-Difluoro-6-methoxy-1,2,3,4-tetrahydronaphthalen-7-yl)methyl)amino-2-phenylpiperidine dihydrochloride (Compound 98)

(i) 6-Methoxy-2,2-difluoro-1,2,3,4-tetrahydronaphthalene (Compound 95)

To a stirred solution of 6-Methoxy-2-tetralone (352 mg, 2.00 mmol) in dry CHCl₃ (5 ml) was added diethylamino-sulfur trifluoride (366 mg, 2.27 mmol) at room temperature. The reaction mixture was stirred at reflux temperature for 7 h. The mixture was diluted with sat. NaHCO₃ and extracted with CH₂Cl₂. The combined solution was dried(MgSO4) and concentrated in vacuo to give crude product as a brown oil. The crude product was purified by column chromatography on silica gel with hexane-ethyl acetate(25:1) to give Compound 95 (181 mg, 46%) as a yellow oil.

¹H-NMR (CDCl₃) 7.00 (d, J=8.1 Hz, 1H), 6.75 (dd, J=8.4, 2.9 Hz, 1H), 6.68 (d, J=2.6 Hz, 1H), 3.78 (s, 3H), 3.18 (t, J=15.0 Hz, 2H), 2.98 (t, J=7.0 Hz, 2H), 2.27–2.11 (m, 2H).

(ii) 7-Formyl-6-methoxy-2,2-difluoro-1,2,3,4-tetrahydronaphthalene(Compound96)

To a stirred solution of Compound 95 (90 mg, 0.45 mmol) in dry CH₂Cl₂ (10 ml) was added TiCl₄ (104 mg, 0.55 mmol) via a syringe at −78° C. After 15 min, to this was added dichloromethyl methyl ether (636 mg, 0.55 mmol) at same temperature. The reaction mixture was stirred at −78° C. for 2 h. The mixture was diluted with water (10 ml) with ice-cooling and stirred at room temperature for 15 min. The organic layer was separated and the aqueous layer was extracted with CH₂Cl₂. The combined solution was dried (MgSO₄), and concentrated in vacuo to give crude product as a yellow oil. The crude product was purified by column chromatography on silica gel with hexane-ethyl acetate (10:1) to give Compound 96 (44 mg, 43%) as a yellow oil.

¹H-NMR (CDCl₃) 10.39 (s, 1H), 7.56 (s, 1H), 6.75 (s, 1H), 3.91 (s, 3H), 3.21 (t, J=14.7 Hz, 2H), 3.05 (t, J=7.0 Hz, 2H), 2.30–2.15 (m, 2H).

(iii) (2S, 3S)-1-tert-Butoxycarbonyl-3-((2,2-difluoro-6-methoxy-1,2,3,4-tetrahydronaphthalen-7-yl)methyl)amino-2-phenylpiperidine (Compound 97)

This compound was prepared from Compound 96 and Compound 12 in the same manner of Compound 13.

¹H-NMR (CDCl₃) 7.58 (d, J=7.3 Hz, 2H), 7.34–7.25 (m, 3H), 6.90 (s, 1H), 6.56 (s, 1H), 5.49 (s,1H), 3.97–3.71 (m, 3H), 3.68 (s, 3H), 3.14 (t, J=15.0 Hz, 2H), 3.08–2.93 (m, 4H), 2.24–2.09 (m, 2H), 1.81–1.53 (m, 4H), 1.42 (s, 9H).

(iv) (2S, 3S)-3-((2,2-Difluoro-6-methoxy-1,2,3,4-tetrahydronaphthalen-7-yl)methyl)amino-2-phenylpiperidine dihydrochloride (Compound 98)

This compound was prepared from Compound 97 in the same manner of Compound 60.

$^1$H-NMR (CDCl$_3$) 7.35–7.29 (m, 5H), 6.64 (s, 1H), 6.43 (s, 1H), 3.94 (s,1H), 3.71–3.27 (m, 3H), 3.44 (s, 3H), 3.07 (t, J=15.4 Hz, 2H), 2.93 (t, J=6.9 Hz, 2H), 2.88–2.77 (m, 2H), 2.25–1.90 (m, 4H), 1.75–1.43 (m, 2H).

EXAMPLE 20

Preparation of (2S, 3S)-3-(2-Methoxy-5-(2,2,2-trifluoro-1-hydroxy-1-(trifluoromethyl)ethyl)benzyl)amino-2-phenylpiperidine dihydrochloride (Compound 101)

(i) 4-(2,2,2-trifluoro-1-hydroxy-1-(trifluoromethyl)ethyl)anisole (Compound 99)

This compound was prepared according to the procedures described in Izv. Akad. Nauk SSSR, Ser. Khim., (1979), 659.

(ii) 2-methoxy-5-(2,2,2-trifluoro-1-hydroxy-1-(trifluoromethyl)ethyl)benzaldehyde (Compound 100)

This compound was prepared from Compound 99 in the same manner of Compound 9.

1H-NMR (CDCl$_3$) 10.47 (s, 1H), 8.29–7.03 (m, 3H), 4.05 (s, 1H), 3.99 (s, 3H)

(iii) (2S, 3S)-2-methoxy-3-(5-(2,2,2-trifluoro-1-hydroxy-1-(trifluoromethyl)ethyl)benzyl)amino-2-phenylpiperidine dihydrochloride (Compound 101)

This compound was prepared from Compound 100 and Compound 1 in the same manner of Compound 2.

1H-NMR (free base; CDCl$_3$) 7.66–6.65 (m, 8H), 4.02–2.75 (m, 6H), 3.57 (s, 3H), 3.47 (s, 1H), 2.20–1.25 (m, 4H)

mp 299–302° C.

EXAMPLE 21

Preparation of (2S, 3S)-3-[5-[(1-Chloro-1-(trifluoromethyl)ethyl]-2-methoxybenzylamino]-2-phenylpiperidine dihydrochloride (Compound 105)

(i) 5-[(1-Chloro-1-(trifluoromethyl)ethyl]-2-methoxybenzaldehyde (Compound 102)

This compound was prepared from Compound 69 in the same manner of Compound 46.

$^1$H-NMR(CDCl$_3$) 10.47(s, 1H), 8.06(d, J=2.9 Hz, 1H), 7.97–7.87(m, 1H), 7.05(d, J=8.8 Hz, 1H), 3.98(s, 3H), 2.15(s, 3H)

(ii) (2S, 3S)-1-tert-Butoxycarbonyl-3-[5-[(1-Chloro-1-(trifluoromethyl)ethyl]-2-methoxybenzylamino]-2-phenylpiperidine (Compound 103)

This compound was prepared from Compound 12 and Compound 102 in the same manner of Compound 26. This was employed in the next step without further purification.

(iii) (2S, 3S)-3-[5-[(1-Chloro-1-(trifluoromethyl)ethyl]-2-methoxybenzylamino]-2-phenylpiperidine (Compound 104)

This compound was prepared from Compound 103 in the same manner of Compound 27.

$^1$H-NMR(CDCl$_3$) 7.50–7.15(m, 7H), 6.72–6.62(m, 1H), 3.89(d, J=2.2 Hz, 1H), 3.75–3.60(m, 1H), 3.51(s, 3H), 3.40(d, J=14.3 Hz, 1H), 3.35–3.21(m, 1H), 2.90–2.71(m, 2H), 2.20–1.80(m, 7H), 1.70–1.35(m, 2H).

(iv) (2S, 3S)-3-[5-[(1-Chloro-1-(trifluoromethyl)ethyl]-2-methoxybenzylamino]-2-phenylpiperidine dihydrochloride (Compound 105)

This compound was prepared from Compound 104 in the same manner of Compound 28.

The chemical structures of the compounds prepared in Examples 1 to 21 are summarized in Table 1.

TABLE 1

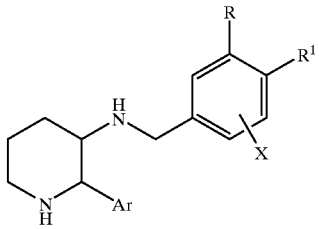

(I)

| Ex. # | Ar | R | R$^1$ | R—R$^1$ | X |
|---|---|---|---|---|---|
| 1 | C$_6$H$_5$ | trifluoromethyl | H | n/a | F |
| 2 | C$_6$H$_5$ | trifluoromethyl | H | n/a | Cl |
| 3 | C$_6$H$_5$ | trifluoromethyl | H | n/a | OCH$_3$ |
| 4 | C$_6$H$_5$ | trifluoromethyl | H | n/a | OC$_6$H$_5$ |
| 5 | C$_6$H$_5$ | 2,2,2-trifluoro-1-(trifluoromethyl)-ethyl | H | n/a | OCH$_3$ |
| 6 | C$_6$H$_5$ | 1,2,2,2-tetrafluoro-1-(trifluoromethyl)-ethyl | H | n/a | OCH$_3$ |
| 7 | C$_6$H$_5$ | 1,1-difluoroethyl | H | n/a | OCF$_3$ |
| 8 | C$_6$H$_5$ | 1,1-difluoroethyl | H | n/a | OCH$_3$ |
| 9 | C$_6$H$_5$ | 1,1,2,2,2-pentafluoroethyl | H | n/a | OCH$_3$ |
| 10 | C$_6$H$_5$ | 2,2,2-trifluoroethyl | H | n/a | OCH$_3$ |
| 11 | C$_6$H$_5$ | 1-(trifluoromethyl)-ethyl | H | n/a | OCH$_3$ |
| 12 | C$_6$H$_5$ | 1,1-dimethyl-4,4,4-trifluoro-2-butynyl | H | n/a | OCH$_3$ |
| 13 | C$_6$H$_5$ | n/a | n/a | CH(CF$_3$)(CH$_2$)$_2$ | OCH$_3$ |
| 14 | C$_6$H$_5$ | 1,1-dimethyl-2,2,2-trifluoroethyl | H | n/a | OCH$_3$ |
| 15 | C$_6$H$_5$ | 2,2,2-trifluoro-1-methyl-1-(trifluoromethyl)ethyl | H | n/a | OCH$_3$ |
| 16 | C$_6$H$_5$ | 2-2-difluoro-1-(trifluoromethyl)ethenyl | H | n/a | OCH$_3$ |
| 17 | C$_6$H$_5$ | 2,2,2-trifluoroethyl | OCH$_3$ | n/a | OCH$_3$ |
| 18 | C$_6$H$_5$ | n/a | n/a | CH(CF$_3$)(CH$_2$)$_3$ | OCH$_3$ |
| 19 | C$_6$H$_5$ | n/a | n/a | CH$_2$CF$_2$(CH$_2$)$_2$ | OCH$_3$ |
| 20 | C$_6$H$_5$ | 2,2,2-trifluoro-1-hydroxy-1-(trifluoromethyl)ethyl | H | n/a | OCH$_3$ |
| 21 | C$_6$H$_5$ | 1-chloro-1-(trifluoromethyl)ethyl | H | n/a | OCH$_3$ |

*X is at 2-position of the benzene ring
**The stereochemistry of 2-aryl and 3-benzylamino is (2S, 3S).

The compounds listed in Tables 2 and 3 are prepared using appropriate starting materials by ways of the methods described in Examples 10, 13, 14, 17, 18 or 19.

TABLE 2

(I)

| Ar | R | R¹ | X |
|---|---|---|---|
| $C_6H_5$ | 3,3,3-trifluoropropyl | H | $OCH_3$ |
| $C_6H_5$ | 1,1-dimethyl-3,3,3-trifluoropropyl | H | $OCH_3$ |
| $C_6H_5$ | 2,2,3,3,3-pentafluoropropyl | H | $OCH_3$ |
| $C_6H_5$ | 1,1-dimethyl-2,2,3,3,3-pentafluoropropyl | H | $OCH_3$ |
| $C_6H_5$ | 3,3,3-trifluoro-1-propenyl | H | $OCH_3$ |
| $C_6H_5$ | 2-trifluoromethyl-3,3,3-trifluoro-1-propenyl | H | $OCH_3$ |
| $C_6H_5$ | 1-methyl-3,3,3-trifluoro-1-propenyl | H | $OCH_3$ |
| $C_6H_5$ | 1-methyl-2-trifluoromethyl-3,3,3-trifluoro-1-propenyl | H | $OCH_3$ |
| $C_6H_5$ | 1-trifluoromethylcyclopropyl | H | $OCH_3$ |
| $C_6H_5$ | 1-trifluoromethylcyclobutyl | H | $OCH_3$ |
| $C_6H_5$ | 1-trifluoromethylcyclopentyl | H | $OCH_3$ |
| $C_6H_5$ | 1-trifluoromethylcyclohexyl | H | $OCH_3$ |
| $C_6H_5$ | 2-(trifluoromethyl)cyclopropyl | H | $OCH_3$ |
| $C_6H_5$ | 2-(trifluoromethyl)cyclobutyl | H | $OCH_3$ |
| $C_6H_5$ | 2-(trifluoromethyl)cyclopentyl | H | $OCH_3$ |
| $C_6H_5$ | 2-(trifluoromethyl)cyclohexyl | H | $OCH_3$ |
| $C_6H_5$ | 2,2,2-trifluoroethyl | F | $OCH_3$ |
| $C_6H_5$ | 1,1,2,2,2-pentafluoroethyl | F | $OCH_3$ |
| $C_6H_5$ | 2,2,2-trifluoroethyl | H | $OCF_3$ |
| $C_6H_5$ | 2,2,2-trifluoroethyl | H | $OCH(CH_3)_2$ |
| $C_6H_5$ | 1,1,2,2,2-pentafluoroethyl | H | $OCF_3$ |
| $C_6H_5$ | 1,1,2,2,2-pentafluoroethyl | H | $OCH(CH_3)_2$ |
| $C_6H_5$ | 1-hydroxy-2,2,2-trifluoroethyl | H | $OCH_3$ |
| $C_6H_5$ | 1-methoxy-2,2,2-trifluoroethyl | H | $OCH_3$ |
| $C_6H_5$ | 2,2-bis(trifluoromethyl)cyclobutyl | H | $OCH_3$ |
| $C_6H_5$ | 1-(trifluoroethyl)ethenyl | H | $OCH_3$ |

*X is at 2-position of the benzene ring
**The stereochemistry of 2-aryl and 3-benzylamino is (2S, 3S).

TABLE 3

(I)

| Ar | R—R¹ | X |
|---|---|---|
| $C_6H_5$ | $CH_2C(CF_3)_2CH_2$ | $OCH_3$ |
| $C_6H_5$ | $CH_2CH(CF_3)CH_2$ | $OCH_3$ |
| $C_6H_5$ | $CH_2C(CF_3)(CH_3)CH_2$ | $OCH_3$ |
| $C_6H_5$ | $CH_2C(CF_3)_2(CH_2)_2$ | $OCH_3$ |
| $C_6H_5$ | $CH_2CH(CF_3)(CH_2)_2$ | $OCH_3$ |
| $C_6H_5$ | $CH(CF_3)CH_2O$ | $OCH_3$ |
| $C_6H_5$ | $C(CF_3)_2(CH_2)_2$ | $OCH_3$ |

TABLE 3-continued (I)

| Ar | R—R¹ | X |
|---|---|---|
| $C_6H_5$ | $C(CF_3)(CH_3)(CH_2)_2$ | $OCH_3$ |
| $C_6H_5$ | $C(CF_3)_2(CH_2)_3$ | $OCH_3$ |
| $C_6H_5$ | $C(CF_3)(CH_3)(CH_2)_3$ | $OCH_3$ |
| $C_6H_5$ | $CH_2CF_2CH_2$ | $OCH_3$ |
| $C_6H_5$ | $CH_2CF_2(CH_2)_2$ | $OCH_3$ |
| $C_6H_5$ | $C(CH_3)_2CF_2CH_2)$ | $OCH_3$ |
| $C_6H_5$ | $C(CH_3)_2CF_2(CH_2)_2$ | $OCH_3$ |

*X is at 2-position of the benzene ring
**The stereochemistry of 2-aryl and 3-benzylamino is (2S, 3S).

What is claimed is:

1. A compound selected from (2S, 3S)-2-phenyl-3-(5-(2,2,2-trifluoro-1-(trifluoromethyl)ethyl-2-methoxybenzyl))aminopiperidine or a salt thereof;

(2S,3S)-3-(2-Methoxy-5-(2,2,2-trifluoroethyl)benzyl)amino-2-phenylpiperidine or a salt thereof;

(2S,3S)-3-(2-Methoxy-5-((1-trifluoromethyl)ethyl)benzyl)amino-2-phenylpiperidine or a salt thereof;

(2S,3S)-3-[5-(1,1-Dimethyl-2,2,2-trifluoroethyl)-2-methoxybenzylamino]-2-phenylpiperidine or a salt thereof; and (2S,3S)-2-Phenyl-3-(5-(2,2,2-trifluoro-1-methyl-1-(trifluoromethyl)ethyl)-2-methoxybenzyl)aminopiperidine or its salts.

2. A compound according to claim 1, which is (2S, 3S)-2-phenyl-3-(5-(2,2,2-trifluoro-1-(trifluoromethyl)ethyl-2-methoxybenzyl))aminopiperidine or a salt thereof.

3. A pharmaceutical composition which comprises a therapeutically effective amount of a compound of claim 1 together with a pharmaceutically acceptable carrier.

4. A method for treating in a mammal a condition characterized by the presence of an excess of substance P activity comprising the administration of a compound according to claim 1.

5. A method according to claim 4 wherein the condition is a gastrointestinal disorder; a central nervous system disorder; an inflammatory disease; emesis; urinary incontinence; pain; migraine; sunburn; diseases, disorders and adverse conditions caused by *Helicobacter pylori*; or angiogenesis.

* * * * *